(12) United States Patent
Piascik et al.

(10) Patent No.: US 9,402,697 B2
(45) Date of Patent: Aug. 2, 2016

(54) MODIFICATION OF CERAMIC SURFACES

(71) Applicant: RESEARCH TRIANGLE INSTITUTE, Research Triangle Park, NC (US)

(72) Inventors: Jeffrey Robert Piascik, Raleigh, NC (US); Brian R. Stoner, Chapel Hill, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 14/395,242

(22) PCT Filed: Apr. 18, 2013

(86) PCT No.: PCT/US2013/037084
§ 371 (c)(1),
(2) Date: Oct. 17, 2014

(87) PCT Pub. No.: WO2013/158829
PCT Pub. Date: Oct. 24, 2013

(65) Prior Publication Data
US 2015/0064654 A1    Mar. 5, 2015

Related U.S. Application Data

(60) Provisional application No. 61/635,480, filed on Apr. 19, 2012.

(51) Int. Cl.
*A61K 6/083* (2006.01)
*A61C 8/00* (2006.01)
(Continued)

(52) U.S. Cl.
CPC .............. *A61C 8/0015* (2013.01); *A01N 25/08* (2013.01); *A01N 55/02* (2013.01); *A61K 6/0067* (2013.01); *A61K 6/0094* (2013.01); *A61K 6/024* (2013.01); *A61K 6/025* (2013.01); *A61K 6/0215* (2013.01);
(Continued)

(58) Field of Classification Search
USPC ................................ 523/116, 118; 433/228.1
See application file for complete search history.

(56) References Cited

U.S. PATENT DOCUMENTS

| 3,066,112 A | 11/1962 | Bowen |
| 3,179,623 A | 4/1965 | Bowen |

(Continued)

FOREIGN PATENT DOCUMENTS

| WO | WO 2011/057055 | 5/2011 |
| WO | WO 2011/152571 | 12/2011 |

OTHER PUBLICATIONS

Aboushelib et al. "Innovations in Bonding to Zirconia-Based Materials: Part I," *Dental Materials*, 2008, vol. 24, pp. 1268-1272.
(Continued)

*Primary Examiner* — Tae H Yoon
(74) *Attorney, Agent, or Firm* — Womble Carlyle Sandridge & Rice, LLP

(57) ABSTRACT

A fluoride treated ceramic material is provided, the ceramic material comprising fluorinated metal oxide on its surface. A method for the preparation of such treated ceramics is also provided, the method involving exposure of the ceramic to a fluorine-containing reagent. The ceramic materials can be further functionalized so as to bond to functional ligands and/or resins. The ceramic materials can be, for example, ceramic medical implants or particulate ceramic, which can be incorporated within dental and/or orthopedic composites.

33 Claims, 12 Drawing Sheets

(51) Int. Cl.
*A61K 6/00* (2006.01)
*A61K 6/02* (2006.01)
*A61L 27/10* (2006.01)
*A61L 27/44* (2006.01)
*A61L 27/54* (2006.01)
*A01N 25/08* (2006.01)
*A01N 55/02* (2006.01)

(52) U.S. Cl.
CPC ............ *A61K 6/0225* (2013.01); *A61K 6/0235* (2013.01); *A61K 6/0255* (2013.01); *A61K 6/0835* (2013.01); *A61L 27/10* (2013.01); *A61L 27/446* (2013.01); *A61L 27/54* (2013.01); *A61L 2300/104* (2013.01); *A61L 2300/106* (2013.01); *A61L 2300/206* (2013.01); *A61L 2300/406* (2013.01); *A61L 2400/18* (2013.01); *A61L 2430/12* (2013.01); *Y10T 29/49885* (2015.01)

(56) References Cited

U.S. PATENT DOCUMENTS

| | | | |
|---|---|---|---|
| 3,629,187 | A | 12/1971 | Waller |
| 3,766,132 | A | 10/1973 | Lee et al. |
| 4,002,669 | A | 1/1977 | Gross et al. |
| 4,115,346 | A | 9/1978 | Gross et al. |
| 4,259,117 | A | 3/1981 | Yamauchi et al. |
| 4,292,029 | A | 9/1981 | Craig et al. |
| 4,308,190 | A | 12/1981 | Walkowiak et al. |
| 4,327,014 | A | 4/1982 | Kawahara et al. |
| 4,379,695 | A | 4/1983 | Orlowski et al. |
| 4,404,150 | A | 9/1983 | Tsunekawa et al. |
| 4,503,169 | A | 3/1985 | Randklev |
| 5,969,000 | A | 10/1999 | Yang et al. |
| 6,245,140 | B1 * | 6/2001 | Monden ............... C04B 41/81 106/286.4 |
| 6,553,996 | B2 | 4/2003 | Kittelsen et al. |
| 2002/0169279 | A1 | 11/2002 | Montelaro et al. |
| 2002/0188102 | A1 | 12/2002 | Montelaro et al. |
| 2002/0193462 | A1 | 12/2002 | Angeletakis et al. |
| 2003/0036627 | A1 | 2/2003 | Montelaro et al. |
| 2003/0114554 | A1 | 6/2003 | Ario et al. |
| 2004/0126409 | A1 | 7/2004 | Wilcox et al. |
| 2005/0252415 | A1 | 11/2005 | Budd et al. |
| 2006/0154206 | A1 | 7/2006 | Petersson et al. |
| 2008/0063688 | A1 | 3/2008 | Wilcox et al. |
| 2010/0150985 | A1 | 6/2010 | Just et al. |
| 2011/0060172 | A1 * | 3/2011 | Wang ............... B01J 21/04 570/176 |
| 2013/0108708 | A1 * | 5/2013 | Xu ............... A61K 6/0008 424/618 |

OTHER PUBLICATIONS

Aboushelib et al. "Innovations in Bonding to Zirconia-Based Materials: Part II: Focusing on Chemical Interactions," *Dental Materials*, 2009, vol. 25, pp. 989-995.
Nandini, "Indirect Resin Composites," *J. Conservative Dent.*, 2010, 13(4), pp. 184-194. www.ncbi.nlm.nih.gov/pmc/articles/PMC3010022/.
Pantano et al., "Hydrolysis Reactions at the Surface of Fluorozirconate Glass," *J. Am. Ceram. Soc.*, 1988, vol. 71(7), pp. 577-581.
Piascik et al., "Surface Modification for Enhanced Silanation of Zirconia Ceramics," *Dental Materials*, 2009, vol. 25, pp. 1116-1121.
Piascik et al., "Development of a Novel Surface Modification for Improved Bonding to Zirconia," *Dental Materials*, 2011, vol. 27, No. 5, pp. e99-e105.
Piascik et al., "Enhanced Bonding Between YSZ Surfaces Using a Gas-Phase Fluorination Pretreatment," *J. Biomed Res B: Appl Biomater*, 2011, 98B(1): 114-119.
Piascik et al., "Surface Fluorination of Zirconia: Adhesive Bond Strength Comparison to Commercial Primers," *Dental Materials*, 2012, vol. 28, pp. 604-608.
Sevinç et al., "Antibacterial Activity of Dental Compsites Containing Zinc Oxide Nanoparticles," *J. Biomed. Mater. Res. B. Appl. Biomater.* 2010, 94(1):22-31.
Slots, "Selection of Antimicrobial Agents in Periodontal Therapy," *J. Periodontal Res.*, 2002, 37: pp. 389-398.
Wolter et al., "Characterization of Plasma Fluorinated Zirconia for Dental Applications by X-Ray Photoelevtron Spectroscopy," *Applied Surface Science*, 2011, vol. 257(23), pp. 10177-10182.
www.doctorspiller.com/Composites/resin-glass_composites.htm, Doctor Spiller.Com, "Resin-Glass Composites," 2012, pp. 1-4.
www.doctorspiller.com/Composites/dental_materials.htm, Doctor Spiller.Com, "Dental Composites: An Overview," 2012, pp. 1-3.
www.doctorspiller.com/Composites/types_of_composites.htm, Doctor Spiller.Com, "Types of Composites," 2012, pp. 1-6.

* cited by examiner (A)

(B) 2 – 2min Exposure Contact angle - 6°

(C) 1 – Untreated Contact angle - 58°

(A)

(B)

(A)

(B)

(A)

(B)

(C)

(A)

(B)

MODIFICATION OF CERAMIC SURFACES

CROSS-REFERNECE TO RELATED APPLICATIONS

The present application is a U.S. National Stage of International Patent Application PCT/US2013/037084, filed Apr. 18, 2013, and claim priority to U.S. Provisional Patent Application No. 61/635,480, filed Apr. 19, 2012. The disclosures of each of the applications noted above are incorporated herein by reference in their entirety.

FIELD OF THE INVENTION

The invention is related to methods for modifying ceramic surfaces for use in biomedical implants and composite materials. It is also related to ceramic surfaces that have been modified to endow them with certain advantageous properties.

BACKGROUND OF THE INVENTION

Statistics show that nearly 70% of adults ages 35 to 44 have lost at least one permanent tooth to an accident, gum disease, a failed root canal, or tooth decay. Tooth decay (i.e., dental caries) in particular, is widespread and is considered to be one of the most common diseases in the world. Tooth decay generally results from bacteria that cause demineralization of the structure of the tooth. Although very small carious lesions can remineralize, in order to stop progression of tooth decay, it is typically necessary to remove any decayed dental material.

The removed dental material is generally replaced with some sort of dental restorative to restore the tooth's functionality. In some cases, a restorative material must simply be filled into the open space remaining within the tooth structure (e.g., in the form of a paste or viscous liquid) and cured in place to provide a hardened, filled surface. Such restorative materials can include dental amalgam, porcelain, gold, and composite resins (i.e., "direct restorative composites," or "DRCs"). In other cases, restorative materials (e.g., composite resins) can be used to form "indirect restorative composites," or "IRCs." These types of restorative materials are prepared using an impression of the tooth structure, applied to the remaining tooth structure, and attached in place. Exemplary IRCs include veneers (inlays, onlays), crowns, bridges, and prefabricated teeth. Composites can also can supplement and complement other types of restorations (e.g., ceramic restorations). For example, composite materials can be used in attaching two or more materials together (e.g., in the cementation of crowns).

For both direct and indirect restoratives, composites, or "composite resins" are in wide use due to their aesthetic and mechanical properties. Composite resins generally comprise a resin-based oligomer matrix and an inorganic filler as a strengthening agent. The properties of the filler can vary; for example, the chemical makeup of the inorganic filler or fillers can be selected from glass, quartz, ceramic, or a combination thereof, among other materials. Further, composites may be microfilled/dispersion reinforced composites (comprising filler with an average particle size of about 1 µm or less), macrofilled/particulate composites (having a particle size of about 1 µm or greater) or hybrid composites (having both microfillers and macrofillers). Exemplary fillers and composites are provided in U.S. Pat. No. 3,066,112 to Bowen; U.S. Pat. No. 3,230,184 to Alford; U.S. Pat. No. 3,452,437 to Chang; U.S. Pat. No. 3,792,531 to Rossi; U.S. Pat. No. 3,973,972 to Muller; U.S. Pat. No. 3,975,203 to Dietz; U.S. Pat. No. 4,215,033 to Bowen; and U.S. Patent Application No. 2002/0193462 to Angeletakis et al., which are incorporated herein by reference.

Restorative materials in general can sometimes exhibit somewhat poor mechanical strength and/or wear resistance and thus are not as commonly used in larger (especially posterior) restorations. The mechanical strength of composites can be increased by including a filler comprising a high strength ceramic (e.g., a zirconia or titania-based ceramic). However, high strength ceramics tend to experience failure in use due to little or no binding between the high strength ceramic filler and the resin matrix of the composite material. Further, in some composites generally, plaque accumulation and biofilm growth have been noted to result in recurrent tooth decay (i.e., secondary caries). In order to address this concern, some research has been conducted on incorporating antibacterial compounds into dental composites. See, for example, Sevinc et al., *J. Biomed. Mater. Res. B. Appl. Biomater.* 2010 July; 94(1): 22-31, which is incorporated herein by reference.

It would be advantageous to provide further composite materials with advantageous properties, such as increased mechanical strength, decreased wear resistance, decreased failure, and/or antimicrobial properties.

BRIEF SUMMARY OF THE INVENTION

In one aspect of the present invention is provided a ceramic surface (e.g., a ceramic implant or a particulate ceramic), wherein the surface comprises a fluorinated metal oxide. The ceramic surface may comprise, for example, zirconia, alumina, titania, chromium oxide, or a combination thereof. In some embodiments, the fluorinated metal oxide comprises a mixture of metal oxyfluoride and metal fluoride phases.

In certain embodiments, a dental composite material comprising a polymerizable resin and a particulate filler dispersed therein is provided, wherein the filler comprises ceramic particles having a fluorinated metal oxide surface. The fluorinated metal oxide can, in certain embodiments, comprise a mixture of metal oxyfluoride and metal fluoride phases. The chemical makeup of the ceramic particles can vary, and in some embodiments, the ceramic particles comprise a material selected from the group consisting of zirconia, alumina, titania, and chromium-oxide-based materials.

In some embodiments, at least a portion of the ceramic particles further comprise a silane coupling agent overlying the fluorinated metal oxide surface. The silane coupling agent may be, for example, 3-methacryloyloxypropyltrimethoxysilane, 3-trimethoxysilylpropylmethacrylate, 3-acryloyloxypropyltrimethoxysilane, 3-isocyanatopropyltriethoxysilane, N-[3-(trimethoxysilyl)propylethylenediamine], 3-mercaptopropyltrimethoxysilane, bis-[3-(triethoxysilyl)propyl]polysulfide, or a combination thereof.

In certain embodiments, the polymerizable resin of the dental composite material comprises a methacrylate or dimethacrylate resin-based oligomer matrix. Exemplary resins include, but are not limited to, resins selected from the group consisting of bisphenol-A glycidyl methacrylate, urethane dimethacrylate, triethylene glycol dimethacrylate, and copolymers, mixtures, and derivatives thereof. At least a portion of the ceramic particles of the dental composite material may, in some embodiments, be coupled to the polymerizable resin. For example, in some embodiments, ceramic particles can be indirectly coupled by bonding between a moiety on a silane coupling agent and a moiety on the polymerizable resin.

At least a portion of the ceramic particles of the dental composite material may, in some embodiments, comprise an antimicrobial agent attached thereto. For example, in some embodiments, the antimicrobial agent can be attached indirectly to the ceramic particles by means of a coupling agent overlying the fluorinated metal oxide surface. In certain embodiments, the coupling agent comprises a silane coupling agent. In such cases, the antimicrobial agent can be attached to the particle by bonding (e.g., covalent bonding) between a moiety on the silane coupling agent and a moiety on the antimicrobial agent.

The antimicrobial agent may, for example, comprise an antibiotic. Exemplary antibiotics include, but are not limited to, silver acetate, silver benzoate, silver carbonate, silver ionate, silver iodide, silver lactate, silver laureate, silver nitrate, silver oxide, silver palmitate, silver protein, silver sulfadiazine, calcium oxide, calcium hydroxide, magnesium oxide, magnesium hydroxide, barium oxide, barium hydroxide, strontium oxide, strontium hydroxide alkali, chlorhexidine; 5-chloro-2(2-4-dichlorophenoxy)phenol), polyhexamethylenebiguanide hydrochloride (PHMB), doxycycline, metronidazole, thymol, encalypol, methyl salicylate, 4'-sulfamoyl-sulfanilanilide, 3-amino-6-(2-(5-nitro-2-furyl)vinyl) pyridiazine, transpseudomonic acid, xanthomycin, alpha-amino-p-toluene sulfonamide, alpha-azido benzyl penicillin, penicillin O, penicillin N, monopropionyl erythromycin, erythromycin 9(O-((2-methoxyethoxy)methyl)oxime; 1,1'-hexamethylene bis(5-(p-chlorophenyl)biguanide), cetyl pyridinium chloride; benzalkonium chloride, cetyl pyridinium bromide, 2,4,4'-trichloro-2'-hydroxy-diphenyl ether, and antimicrobial peptides, and combinations thereof.

In another aspect of the present invention is provided a ceramic material comprising a fluorinated metal oxide surface with one or more antimicrobial agents attached thereto. In some embodiments, the antimicrobial agents can be attached indirectly to the ceramic material by means of a coupling agent overlying the fluorinated metal oxide surface. The coupling agent can be, for example, a silane coupling agent. The ceramic can be, for example, a ceramic implant or a particulate ceramic. In some embodiments, the ceramic material comprises a material selected from the group consisting of zirconia, alumina, titania, and chromium-oxide-based materials.

In a further aspect of the invention is provided a method of preparing a dental composite material, comprising: providing particulate ceramic comprising surfaces formed of a material comprising available hydroxyl groups; treating the particulate ceramic with a fluorine-containing reagent to provide a fluorinated metal oxide on the particulate ceramic surfaces; and dispersing the particulate ceramic within a polymerizable resin matrix. The treating step can vary. For example, in certain embodiments, the treating step comprises plasma treatment and may, in some embodiments, comprise physical roughening or chemical etching of the implant surface prior to or at the same time as treating the implant with the fluorine-containing reagent. In some embodiments, the fluorine-containing reagent is sulfur hexafluoride ($SF_6$).

In some embodiments, the method can further comprise attaching one or more antimicrobial agents to the fluorinated metal surface. The attaching can, in some embodiments, comprise attaching the one or more antimicrobial agents indirectly to the fluorinated metal oxide surface by means of a coupling agent overlying the fluorinated metal oxide surface. The method may, in certain embodiments, comprise reacting the particle surfaces having the fluorinated metal oxide thereon with a coupling agent (e.g., a silane coupling agent). In some embodiments, the method comprises coupling the coupling agent to a polymerizable resin matrix. The method can, in certain embodiments, comprise attaching one or more antimicrobial agents to a portion of the fluorinated metal oxide surfaces and coupling a portion of the fluorinated metal oxide surfaces to the polymerizable resin matrices. For example, the method may comprises coupling a portion of the silane coupling agents to an antimicrobial agent and a portion of the silane coupling agents to the polymerizable resin.

In another aspect of the invention is provided a method of preparing the surface of a ceramic implant, comprising: providing a ceramic implant comprising a surface formed of a material comprising available hydroxyl groups; treating the ceramic implant with a fluorine-containing reagent to provide a fluorinated metal oxide on the surface; and attaching one or more antimicrobial agents to at least a portion of the fluorinated metal oxide. This method may, in some embodiments, further comprise applying dental cement to attach at least a portion of the fluorinated metal oxide to a dental component selected from the group consisting of dental implants, crowns, bridges, fillings, veneers, inlays, onlays, endodontic devices, or orthodontic brackets. These dental components can comprise surfaces comprising, for example, natural tooth, metal, porcelain fused to metal, porcelain, ceramic, resin, or a combination thereof.

BRIEF DESCRIPTION OF THE SEVERAL VIEWS OF THE DRAWINGS

Figure 1:
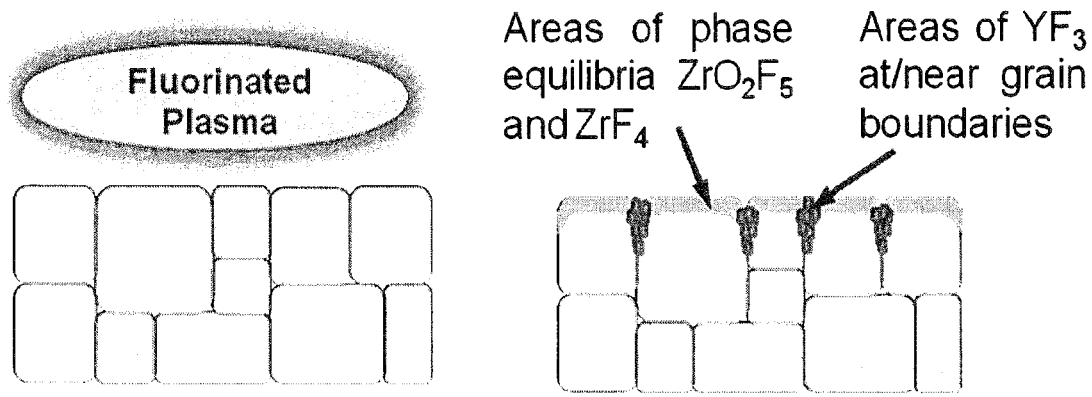
Figure 2:
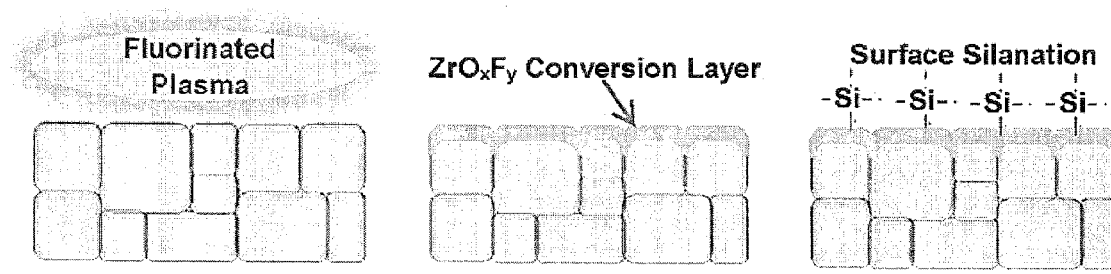
Figure 3:
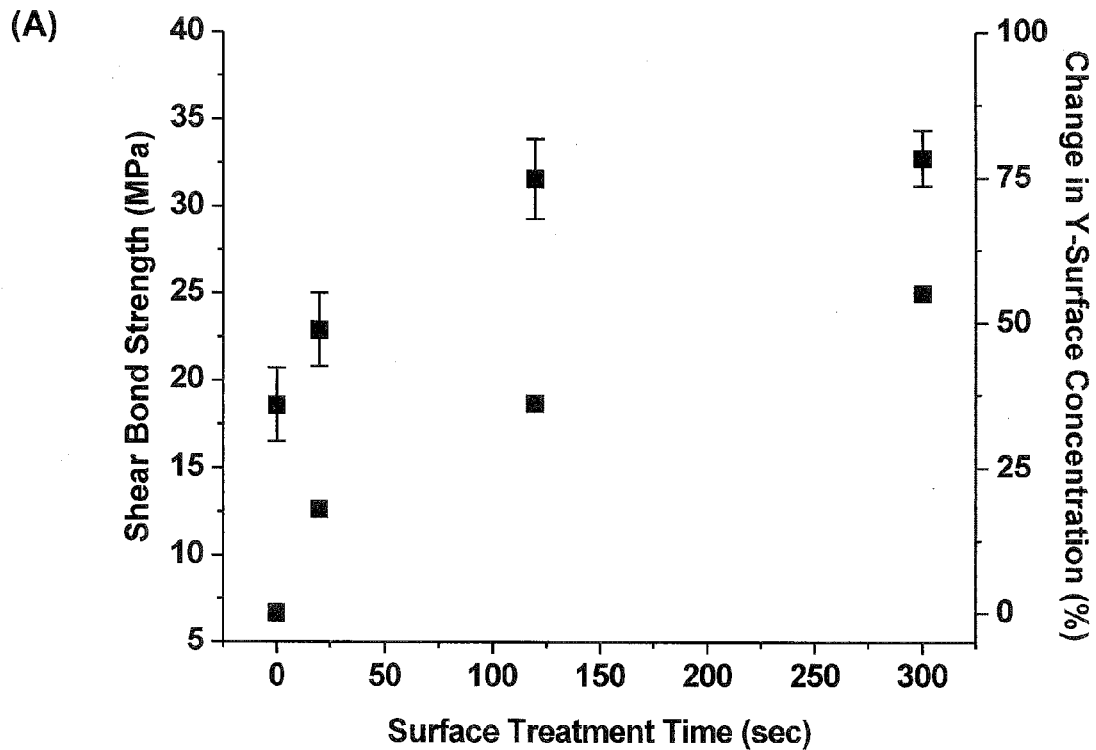
Figure 3:
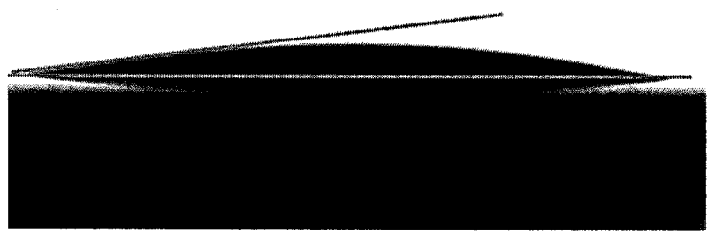
Figure 3:
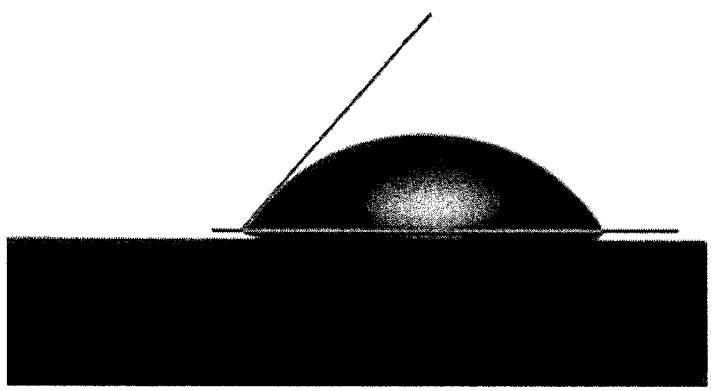
Figure 4:
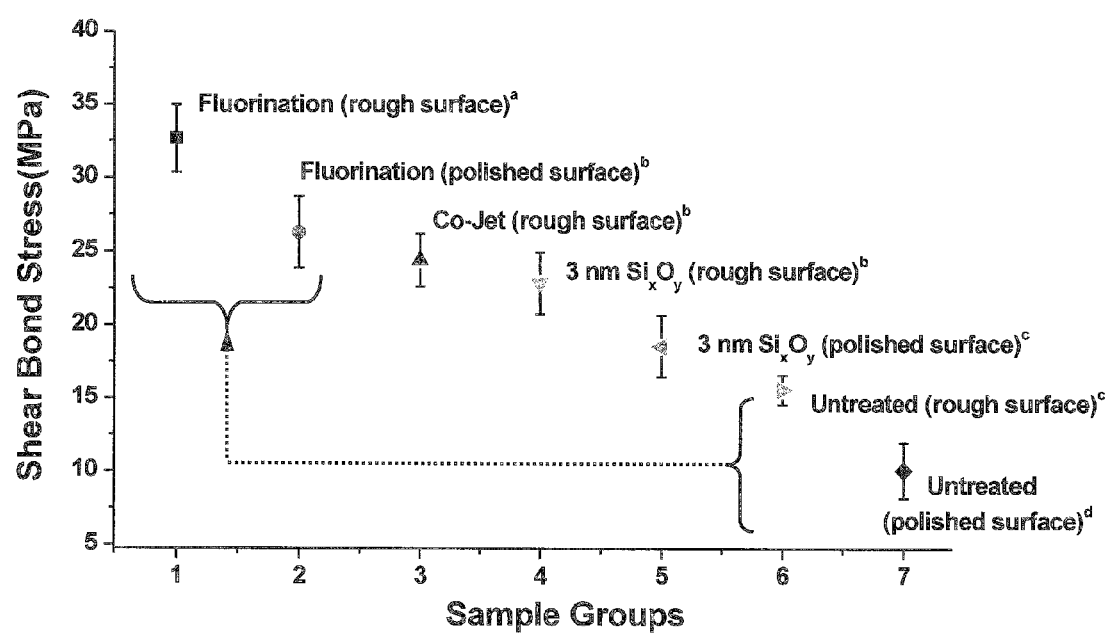
Figure 7:
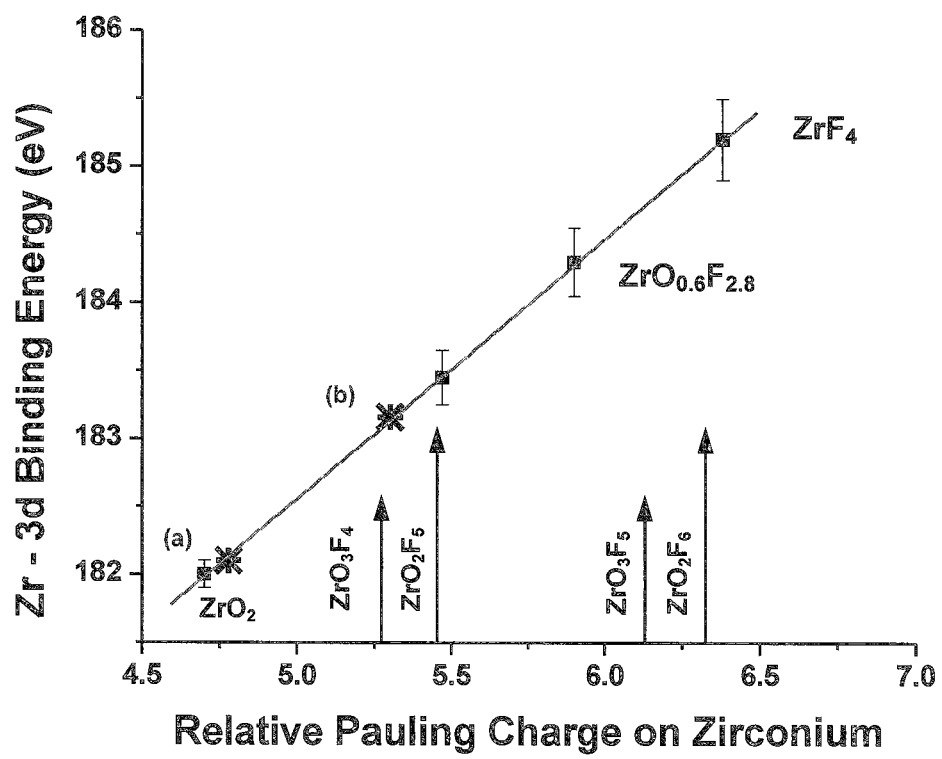
Figure 8:
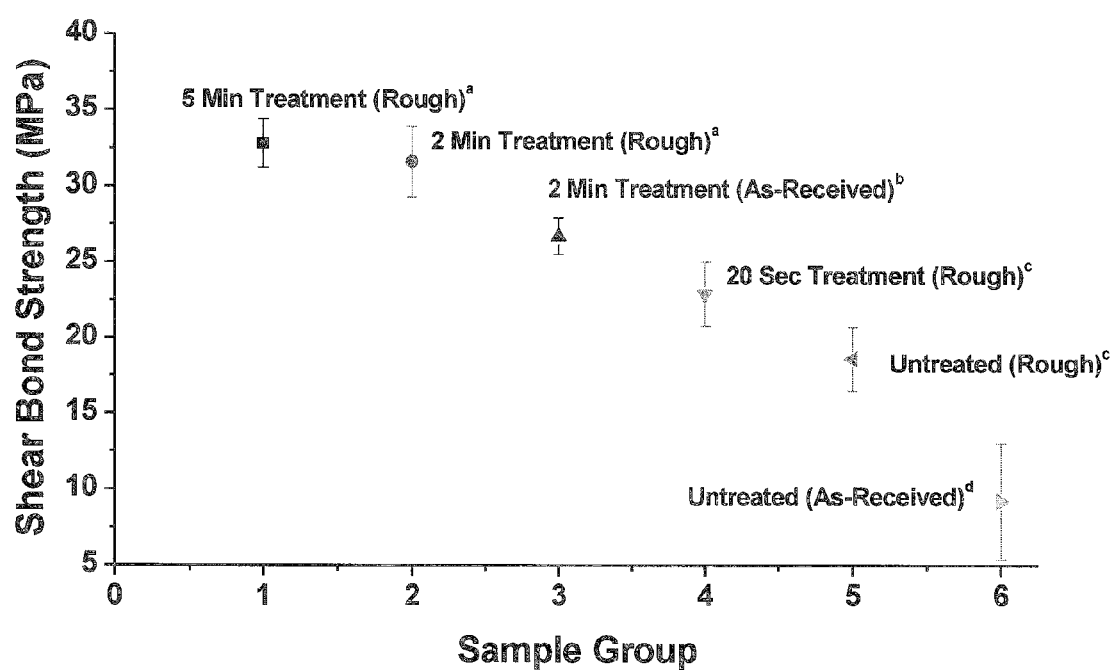
Figure 9:
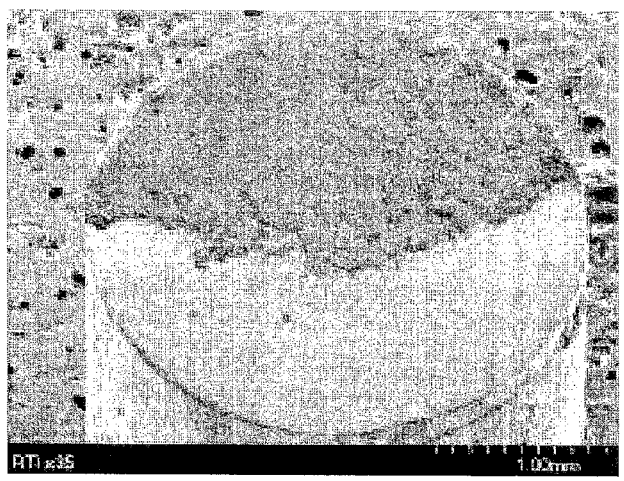
Figure 9:
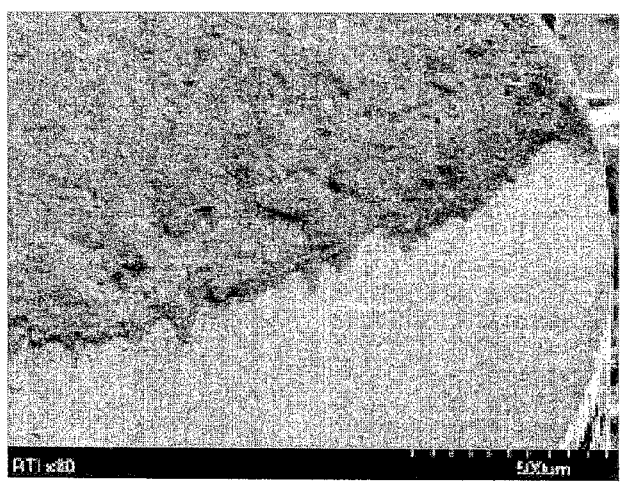
Figure 9:
Figure 10:
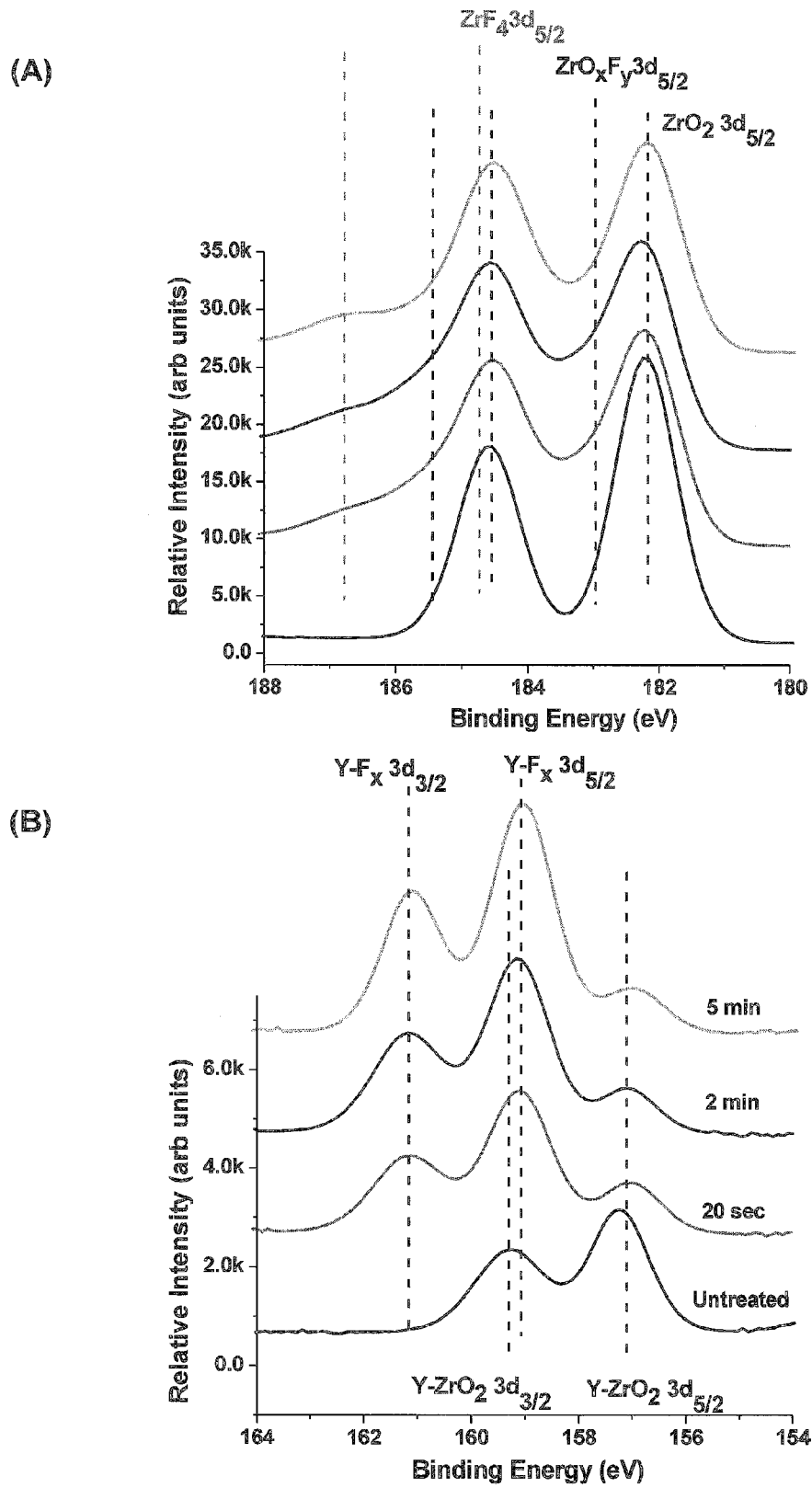
Figure 11:
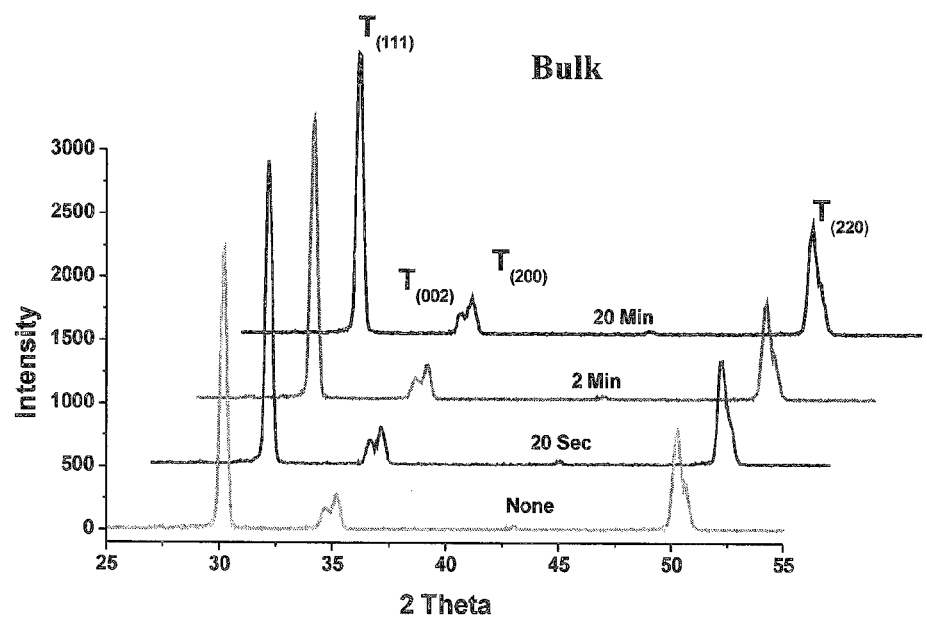
Figure 11:
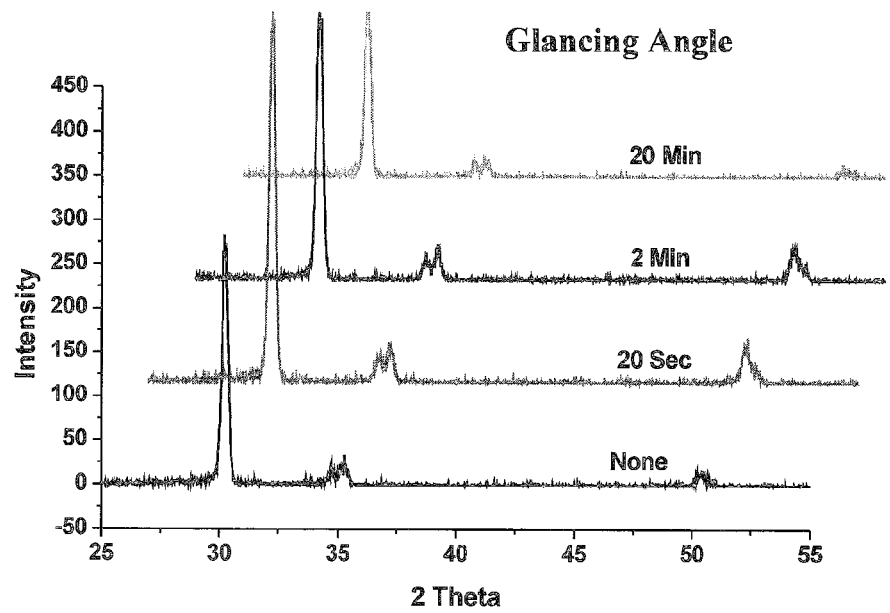
Figure 12:
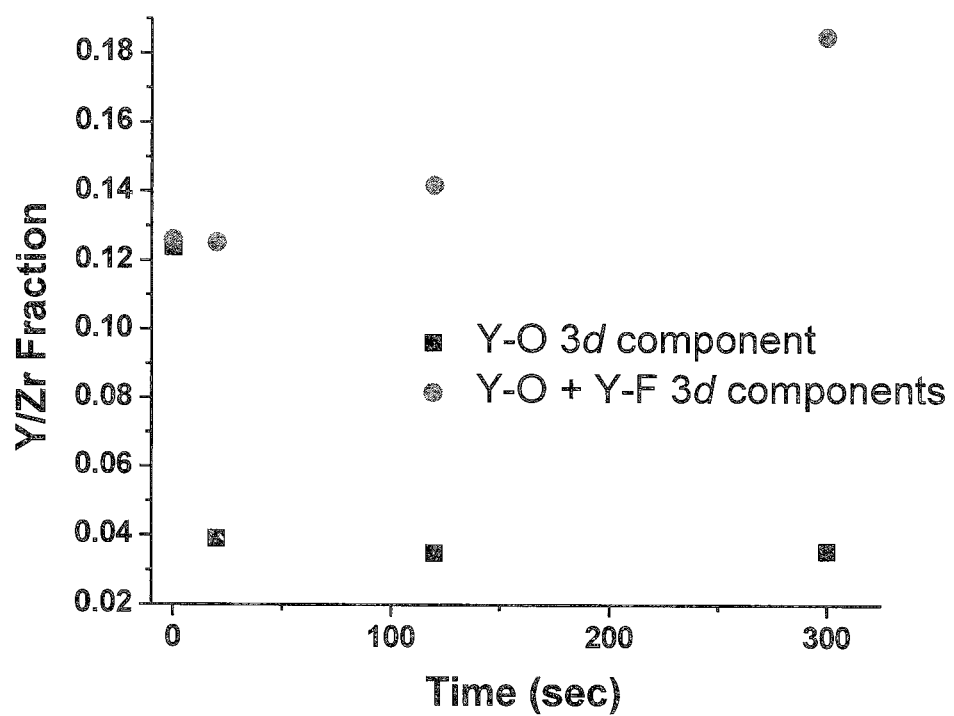

Having thus described the invention in general terms, reference will now be made to the accompanying drawings, which are not necessarily drawn to scale, and wherein:

FIG. 1 is a schematic of fluorinated plasma ($SF_6$ as source gas) induced phase conversion on an yttrium-stabilized zirconia surface;

FIG. 2 is a schematic representation of the plasma surface modification process on a zirconia surface;

FIG. 3(A) is a graph showing the relationship of shear bond strength and change in Y-surface concentration as a function of plasma treatment time;

FIGS. 3(B) and 3(C) are contact angle images of a 2-minute treated and an untreated control specimen, respectively;

FIG. 4 is a graph showing shear bond stress values for various modified and unmodified zirconia surfaces;

FIGS. 5(A) and 5(B) are SEM micrographs at different magnifications of a fluorinated (polished) surface with an adhesive/cohesive failure mode;

FIGS. 6(A) and 6(B) are XPS core scans of the Zr 3d doublet of an untreated zirconia sample (FIG. 6(A)) and a fluorinated zirconia sample (FIG. 6(B));

FIG. 7 is a graph depicting the relationship between Zr 3d binding energy and the Pauling charge on $Zr^+$-cation, with added data points of Zr 3d binding energies measured via XPS from untreated and fluorinated zirconia specimens;

FIG. 8 is a graph showing shear bond strength values for various modified and unmodified yttrium-stabilized zirconia surfaces;

FIGS. 9(A), 9(B), and 9(C) are scanning electron micrographs at different magnifications of a 2 min (roughened) fluorinated specimen failure surface (dark regions are resin cement and white regions are yttria-stabilized zirconia surface);

FIGS. 10(A) and 10(B) show XPS analysis of the Zr-3d (FIG. 10(A)) and the Y-3d spectra (FIG. 10(B)) as a function of fluorination plasma treatment time;

FIGS. 11(A) and 11(B) are X-ray diffraction scans of bulk material (FIG. 11(A)) and 2° glancing angle (FIG. 11(B)); and FIG. 12 is a plot of Y/Zr concentration versus time comparing the relative yttrium to zirconium levels and respective bonding components for XPS deconvolution.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

I. Definitions

"Medical implant" as used herein means any physical object that can be implanted into the body or which comes in direct contact with the body. Medical implants that may be used according to the methods of the present invention include, but are not limited to, dental components, including dental implants, restoratives, and orthodontic devices, as well as orthopedic devices and implants. Any medical implant that may be affixed to another surface or device by a resin or cement may be surface-treated according to the present invention.

The medical implant can comprise any surface material comprising available hydroxyl groups on its surface. For example, the medical implant may be a metal, which inherently has a metal oxide layer on its surface, a polymer or copolymer, or a metal oxide. In certain embodiments, the metal implant comprises a refractory metal oxide. In one embodiment, the medical implant comprises a ceramic material. In some embodiments, the medical implant may comprise zirconia, alumina, titania, or chromium-oxide-based material or a combination thereof. In certain embodiments wherein the medical implant comprises a ceramic, the ceramic may be unstabilized (i.e., pure) or may comprise a stabilized material, e.g., a fully or partially stabilized ceramic material. For example, in specific embodiments, the ceramic may be stabilized with an oxide (e.g., yttrium oxide, magnesium oxide, calcium oxide, and/or cerium(III)oxide). In certain specific embodiments, the medical implant comprises yttria-stabilized zirconia (YSZ). In another embodiment, the medical implant may be a metallic device that is surface passivated with an oxide film. For example, the surface of the metal implant may comprise titanium oxide on a titanium alloy, or chromium oxide on stainless steel or cobalt chrome.

"Dental implant" as used herein means a post (i.e., a dental abutment) anchored to the jawbone and topped with individual replacement teeth or a bridge that is attached to the post or posts. The term is meant to encompass traditional dental implants as well as mini-dental implants. In some cases where the dental abutment is in the form of natural tooth, the dental implant only comprises the implanted replacement tooth or bridge.

"Restorative" as used herein means any dental component used to restore the function, integrity and/or morphology of any missing tooth structure. Examples of restoratives that may be coated according to the methods described herein include, but are not limited to, crowns, bridges, fillings, veneers, inlays and onlays, as well as endodontic devices including endodontic cones and devices for endodontic root perforation repair.

"Orthodontic device" as used herein means any device intended to prevent and/or correct irregularities of the teeth, particularly spacing of the teeth. Orthodontic devices particularly relevant to the present invention include but are not limited to orthodontic brackets.

"Dental component" as used herein encompasses any component of a dental implant or a restorative or an orthodontic device and can even include, in certain embodiments, natural tooth.

"Orthopedic device" or "orthopedic implant" as used herein means a device that replaces a part or function of the body. Orthopedic devices include but are not limited to devices adapted to form artificial joints, including hips, knees, and elbows.

"Composite" as used herein means a material comprising a resin matrix (e.g., a polymerizable resin matrix) and one or more fillers. Although the disclosure relates primarily to dental composites, it is noted that the composites described herein may be relevant to other applications as well (e.g., orthopedic composites) and these other applications are also intended to be encompassed herein. The inventive composites provided herein generally comprise one or more ceramic particulate fillers. The composites may further comprise one or more additional fillers as well as components such as initiators, catalysts, surfactants, pH adjusters, buffers, and/or pigments.

"Nanoparticle" as used herein has its common meaning, and generally refers to a particle with a diameter of less than about 100 nm (generally about 1 nm to about 100 nm). A given sample of nanoparticles generally has an average diameter somewhere within this range. Nanoparticles can be irregular or regular in shape and can be, for example, spherical, fibrous, or flaky in shape.

II. Dental Composites

In one aspect of the invention is provided a composite material. Although the discussion herein focuses on composite materials for use in dental applications, it is noted that the materials described herein may be useful in other applications as well (e.g., as orthopedic composite materials). Such other applications are also intended to be encompassed herein, as one of skill in the art would be able to appropriately modify the methods and materials provided herein to adapt the composite material for the desired application.

The composites of the invention generally comprise a polymerizable resin and a filler comprising a particulate ceramic (e.g., a high strength ceramic) dispersed therein. The ceramic is preferably zirconia or alumina but may comprise any material which may have available hydroxyl groups on its surface. In some embodiments, the ceramic may comprise titania, or chromium oxide. In certain specific embodiments, the ceramic comprises yttria-stabilized zirconia (YSZ). The size and shape of the particulate ceramic can vary. For example, in preferred embodiments, the particulate ceramic has an average diameter of less than about 1 micron. The particulate ceramic can comprise, for example, macroparticles, microparticles, and/or nanoparticles. The particle size distribution of the ceramic filler can vary, ranging from a relatively uniform distribution to a distribution that can be represented by a bell curve.

The particulate ceramic advantageously comprises an activated surface comprising a fluorinated metal oxide surface. Although not wishing to be bound by theory, it is thought that the activated surface comprises a metal oxyfluoride (e.g., zirconium oxyfluoride ($ZrO_xF_y$)). The activated surface may be continuous or discontinuous. For example, in certain embodiments, there may be "islands" of fluoride phases on a surface comprising an oxyfluoride phase. For example, the fluorinated metal oxide surface may comprise a mixture of metal oxyfluoride and metal fluoride phases. FIG. 1 shows an example of an activated surface having oxyfluoride and fluoride phases. Thus, in some embodiments, a composite material comprising a polymerizable resin and a filler dispersed therein, wherein the filler comprises a particulate ceramic having fluorinated metal oxide surfaces dispersed therein.

The thickness of the activated surface may vary. For example, in some embodiments, the thickness of the activated surface extends the full diameter of the particle. In such embodiments, the entire particle is converted to comprise a fluorinated metal oxide. In other embodiments, the fluorinated metal oxide is confined to an exterior portion of the particle. For example, the activated surface may comprise a full or partial coating having a thickness of between about 0.5 nm and about half the diameter of the particle, such as between about 1 nm and about 0.5 µm, including between about 5 nm and about 0.25 µm. In certain aspects, this means that the nanoparticle comprises a fluorinated metal oxide surface having a thickness within these ranges.

These activated ceramic particles can be incorporated within a resin, for example, in the same manner as conventional particles. The loading of ceramic particles within the resin can vary and may be, for example, from about 50% to about 95% by volume, such as from about 60% to about 90% by volume, e.g., about 70% to about 90% by volume.

The resin matrix of the dental composite can vary, but is generally initially a polymerizable matrix that can be polymerized (e.g., "cured") to provide a hardened material. The resin can be a self-curing resin (wherein the resin polymerizes upon mixing of certain components) or a light-cured resin (wherein a curing light is used to polymerize reactive moieties present on the resin molecules). Resin matrices that can be used in the composites of the invention can be those used in traditional composite materials. For example, a polymerizable resin matrix may comprise a methacrylate or dimethacrylate resin-based oligomer matrix, such as bisphenol-A glycidyl methacrylate (BIS-GMA), urethane dimethacrylate (UDMA), triethylene glycol dimethacrylate (TEGDMA), or a copolymer, mixture, or derivative thereof. In other embodiments, the resin can be a silorane-based material (e.g., Filtrek™ LS (3M ESPE)) or a dimer-based material (e.g., N'Durance® (Septodont). Exemplary resins are described, for example, in U.S. Pat. No. 3,066,112 to Bowen: U.S. Pat. No. 3,179,623 to Bowen; U.S. Pat. No. 3,539,533 to Lee et al., U.S. Pat. No. 3,629,187 to Waller; U.S. Pat. No. 3,709,866 to Waller; U.S. Pat. No. 3,766,132 to Lee et al.; U.S. Pat. No. 3,860,556 to Taylor; U.S. Pat. No. 4,002,669 to Gross et al.; U.S. Pat. No. 4,115,346 to Gross et al.; U.S. Pat. No. 4,259,117 to Yamauchi et al.; U.S. Pat. No. 4,292,029 to Craig et al.; U.S. Pat. No. 4,308,190 to Walkowiak et al.; U.S. Pat. No. 4,327,014 to Kawahura et al.; U.S. Pat. No. 4,379,695 to Orlowski et al.; U.S. Pat. No. 4,404,150 to Tsunekawa et al.; and U.S. Pat. No. 4,503,169 to Randklev, which are incorporated herein by reference.

The dental composites of the invention can comprise various other components. For example, in some embodiments, one or more additional fillers are included. Other exemplary fillers for composite materials include, but are not limited to, silica, glass (e.g., strontium glass, barium glass, quartz, and borosilicate glass), prepolymerized resin, Kevlar, graphite, mica, wood, hollow glass spheres, and the like. Fillers can be irregular or regular in shape and can be, for example, spherical, fibrous, or flaky in shape. The average particle size of such additional fillers can vary, but typically ranges from a microscopically fine powder (e.g., about 20 to 40 nm in size) to about one micron in size. The particle size distribution of fillers can vary as noted above for the ceramic filler. In certain embodiments, composites can comprise two or more fillers, including the one or more ceramic fillers, wherein each has a different average particle size.

In some embodiments, one or more reagents or other components (e.g., diluents) to tailor physical properties (e.g., flowability) are included within the composites of the invention. In some embodiments, the composite material further comprises a photoinitiator and/or catalyst. Other additional components that can be included within the dental composites of the present invention include, but are not limited to, stabilizers, antioxidants, polymerization enhancers, polymerization inhibitors, and/or pigments.

Composites of varying viscosities are provided according to the invention. Composites can vary in viscosity, e.g., from flowable to packable. A flowable composite flows like a liquid or loose gel, whereas a packable composite is firm to the touch and hard to displace.

In certain embodiments, the particulate ceramic filler of the composites described herein is further functionalized. The method by which the filler is functionalized can vary; however, in certain embodiments, the activated ceramic surface (i.e., the fluorinated metal oxide surface) is advantageously amenable to reaction with various reagents. In some embodiments, the activated ceramic surface is capable of reacting with a silane reagent. For example, in some embodiments, this method is shown generally in FIG. 2. By "silane" or "silane coupling agent" as used herein is meant any compound containing one or more silicon (Si) atoms. Silanes resemble orthoesters, and can be bifunctional. The silanes useful for the present invention are typically bifunctional with dual reactivity. In particular, they are typically able to react with an inorganic substrate (e.g., the activated ceramic surface) and with an organic moiety. Such silanes may include one or more organic functionalities, including but not limited to vinyl, allyl, amino, or isocyanato groups. They also typically contain one or more alkoxy groups, including but not limited to methoxy and ethoxy groups. Silanes may contain one or more other substituents, which may be reactive, including chloride. There may also be an alkyl or alkylene link between the Si and the organic functionality. Silanes may be hydrophilic or hydrophobic, and can also be anionic or cationic. In some embodiments, the silanes are trialkoxysilanes, with three alkoxy groups and one organic functionality. The silanes useful in the present invention include but are not limited to 3-methacryloyloxypropyltrimethoxysilane, 3-trimethoxysilylpropylmethacrylate, 3-acryloyloxypropyltrimethoxysilane, 3-isocyanatopropyltriethoxysilane, N-[3-(trimethoxysilyl)propylethylenediamine], 3-mercaptopropyltrimethoxysilane, and bis-[3-(triethoxysilyl)propyl]polysulfide. There are many silanes that are commercially available. Examples include RelyX™ Ceramic Primer, Monobond™-S, Fusion™, Vectris™ Wetting Agent, Porcelain Repair Primer, Pulpdent™ Silane Bond Enhancer, Silanator™, Cerinate® Primer, Silicoup™ A and B, Ultradent™ Porcelain Etch & Silane, Clearfil™ Porcelain Bond Activator, Clearfil™ Ceramic Primer, Prolong Silane Bond Enhancer, Quadrant™ Porcelain Coupling Agent, Bifix DC™, Bisco™ Porcelain Primer, Cimara™, and ESPE™ Sil.™ Exemplary manufacturers of such silanes include 3M/ESPE, Ivoclar Vivadent, Pulpdent Corporation, Bisco, Inc., Kurayray, Premier Products Company, Mirage, Ultradent Products, Inc., George Taub Products, Cosmedent, VOCO America, Inc., Cavex Holland BV, and Kerr Corporation.

Applying a silane to an inorganic surface typically involves hydrolysis and condensation reactions with the surface. The silane may be applied in polar aqueous alcohol solutions, ethyl acetate, nonpolar solution, or mixtures thereof. For example, the solution may comprise an acetone/ethanol mixture. Preferably, the silane is applied in aqueous alcohol solutions, such as 90-95% ethanol or isopropanol, or more dilute aqueous alcohol solutions comprising about 20 to about 50% ethanol or isopropanol. The OR groups of the silane may be hydrolyzed, becoming OH groups. The one or more alkoxy groups and/or OH groups on the silane may react with free hydroxyl groups on the surface of the inorganic material. The silanes may react with other silanes to form dimers (siloxanes), which may condense to form siloxane oligomers. Such reactions may result in branched hydrophobic siloxane bonds. The siloxane oligomers, siloxane monomers, and/or silanes may react with the inorganic material to form M—O—Si bonds, wherein M is any metal.

Treatment with a silane can, in certain embodiments, endow the composite material with enhanced bonding between the polymerizable resin matrix and the particulate ceramic filler. For example, in certain embodiments, the organic functional end of the silane may react with the resin matrix of the composite (e.g., via covalent bonding, although other methods of bonding may exist). The degree of bonding between the resin matrix and the particulate ceramic filler can vary. In some embodiments, this bonding can result in decreased incidences of failure and/or fracture of the composite material. Thus, the invention, in certain embodiments, encompasses composites (e.g., dental composites) comprising ceramic particles chemically bound within a resin matrix. The means by which the particles are bound is preferably covalent bonding; however, other methods of bonding can occur without departing from the invention.

The resulting composite can be used in any of the applications provided herein (e.g., as a restorative material or to attach two or more dental materials together). In some embodiments, the invention relates to using composites comprising a resin and a filler dispersed therein, wherein the filler comprises a particulate ceramic with fluorinated metal oxide surfaces, and wherein the composite is applied to an open space within a tooth (e.g., in the form of a paste or viscous liquid) and cured in place to provide a hardened, filled surface. The curing can be, for example, accomplished by means of self-curing (wherein the composite cures within a given period of time after mixing the components) or light curing (wherein light of a given wavelength range is required to polymerize reactive moieties present on the resin molecules). In other embodiments, the invention relates to using composites as described herein by preparing an indirect composite (e.g., a veneer (inlay or onlay), crown, bridge, or prefabricated tooth) using an impression of the tooth structure, curing the composite, applying the composite to the remaining tooth structure, and gluing or cementing it in place with standard reagents.

III. Antimicrobial Ceramic Substrates

In certain embodiments, a ceramic substrate is provided that exhibits antimicrobial properties. The ceramic substrate can be any material comprising a ceramic surface. The ceramic substrate can be a bulk material of various sizes and shapes (e.g., a medical implant such as an orthopedic implant or dental implant) or can comprise a particulate material such as described in Part II of the present application.

In certain embodiments, the ceramic comprises an activated surface comprising a fluorinated metal oxide surface (e.g., having metal oxyfluoride and/or metal fluoride phases), which may inherently provide some degree of antimicrobial effects. The activated surface may be continuous or discontinuous, with "islands" of fluoride phases on a surface comprising an oxyfluoride phase in certain embodiments. Although not intended to be limited by theory, it is believed that fluorine phases present on the ceramic surface can exhibit antimicrobial effects because fluorine can function as an antimicrobial agent.

In other embodiments, the antimicrobial effects of a ceramic as described herein can be enhanced by attachment of an antimicrobial reagent (ligand) thereto. The antimicrobial ligand can vary and may be, for example: a low surface energy, fluorinated ligand; a hydrophilic, charged ligand; and/or a biomolecule (e.g., a peptide) functionalized to enable surface conjugation. In certain embodiments, the antimicrobial ligand is an antibiotic.

Useful classes of antimicrobial ligands include, but are not limited to: organohalogens (e.g., chlorinated phenols); antibiotics; metal salts, compounds, and ions; and antimicrobial proteins and peptides. Certain exemplary antimicrobial ligands include, but are not limited to: silver salts, compounds, and ions (e.g., silver acetate, silver benzoate, silver carbonate, silver ionate, silver iodide, silver lactate, silver laureate, silver nitrate, silver oxide, silver palmitate, silver protein, silver sulfadiazine); copper, gold, zinc, and selenium salts, compounds and ions; alkali metal hydroxides and oxides and alkaline earth metal oxides and hydroxides (e.g., calcium oxide, calcium hydroxide, magnesium oxide, magnesium hydroxide, barium oxide, barium hydroxide, strontium oxide, strontium hydroxide alkali); chlorhexidine; 5-chloro-2(2-4-dichlorophenoxy)phenol), polyhexamethylenebiguanide hydrochloride (PHMB), doxycycline, metronidazole, thymol, encalypol, methyl salicylate, 4'-sulfamoyl-sulfanilanide, 3-amino-6-(2-(5-nitro-2-furyl)vinyl) pyridiazine, transpseudomonic acid, xanthomycin, alpha-amino-p-toluene sulfonamide, alpha-azido benzyl penicillin, penicillin O, penicillin N, monopropionyl erythromycin; erythromycin 9(O-((2-methoxyethoxy)methyl)oxime; 1,1'-hexamethylene bis(5-(p-chlorophenyl)biguanide); cetyl pyridinium chloride; benzalkonium chloride; cetyl pyridinium bromide; and 2,4,4'-trichloro-2'-hydroxy-diphenyl ether (Triclosan®). Antimicrobial biomolecules, such as peptides may also be employed and are described, for example, in U.S. Patent Application Publication Nos. 2002/0169279; 2002/0188102; 2003/0036627 to Montelaro et al.; 2004/0126409 and 2008/0063688 to Wilcox et al.; and 2010/0150985 to Just et al., which are incorporated herein by reference. Other antimicrobial agents that may be useful according to the invention include those described in Slots, *J. Periodont. Res.* 2002:37:389-398, which is incorporated herein by reference.

For dental applications in particular, the antimicrobial ligands can be such that they target any type of bacteria that may be present in the oral cavity, but may, in certain embodiments, advantageously inhibit the growth of one or more of the following: *Bacillus cereus varmycoides; Escherichia coli; Pseudomonas aeruginosa; Staphylococcus aureus; Streptococcus mutans; Streptococcus gordonii, Streptococcus oralis, Streptococcus sobrinus, Actinomyces naeslundii, Aspergillus niger; Aureobasidium pullulans; Chaetomium globosum; Gliocladium virens; Penicillum funiculosum; Candida albicans;* and *Saccharomyces cerevisiae.*

Such antimicrobial reagents may attach to the activated ceramic surface directly or may require a coupling agent. For example, in certain embodiments, an antimicrobial agent is attached to a ceramic surface by means of a silane coupling agent as described in Part II of this application. In such embodiments, the free end of the bifunctional silane (e.g., an organic functional end) may be further reacted with an antimicrobial agent. Antimicrobial agents can be attached, for example, by direct reaction between a moiety on the antimicrobial agent and the organic functional end of the silane, by appropriate chemical modification of a moiety on the antimicrobial agent to provide a moiety capable of reacting with the organic functional end of the silane, or by appropriate chemical modification of the organic functional end of the silane to provide a moiety capable of reacting with a moiety on the antimicrobial agent. It is noted that, alternatively, in some embodiments, the incorporation of a functional ligand can be accomplished by pre-functionalizing a silane to attach the antimicrobial agent thereto and attaching the antimicrobial agent-modified silane directly to the ceramic surface.

The degree of functionalization of the ceramic surface with an antimicrobial agent can vary and may be modified to provide varying levels of antimicrobial effects. For example, in some embodiments, a portion of a surface (e.g., a portion of a medical implant surface) may be functionalized with an antimicrobial agent. In some embodiments, a set of ceramic particles are provided, wherein only a portion of the particles comprise antimicrobial agents.

In certain embodiments, a composite material as described in Part II is provided, wherein the composite is provided with antimicrobial properties by the incorporation of ceramic particles that exhibit antimicrobial effects (e.g., either inherently, due to the activation of the ceramic surface, or by attachment of an antimicrobial agent). Varying amounts of antimicrobial-functionalized ceramic particles can be dispersed within the resin. In some embodiments, two or more differently-functionalized types of ceramic particles are incorporated within a single resin. In certain embodiments, a given composite comprises particulate ceramic functionalized with an antimicrobial agent and particulate ceramic capable of reacting with the polymerizable resin matrix. Thus, in such embodiments, the method of the invention comprises reacting an activated ceramic surface with one or more antimicrobial agents, a polymerizable resin matrix, or both one or more antimicrobial agents and a polymerizable resin matrix. Accordingly, in certain embodiments, a particulate ceramic can be provided with both the ability to bind to the resin matrix and antimicrobial properties. Such materials may be capable of providing enhanced mechanical stability due to the bonding of the particles within the resin matrix, as well as providing antimicrobial effects (helping to remedy the concerns of secondary caries upon applying a composite material onto or within a tooth structure as a direct or indirect composite or as a cement-type material holding one or more other materials in place).

Although the discussion herein focuses on the attachment of various antimicrobial agents, it is noted that other functional ligands can be used in place of the antimicrobial agents to endow the resulting ceramic surfaces with various functionalities. Such additional functional ligands are intended to be encompassed herein.

IV. Fluorination Process

In certain embodiments, the method relates to using fluoride treatment to prepare the ceramic surface. Exemplary methods and materials are provided, for example, in International Application No. WO2011/057055 to Piascik et al., which is incorporated herein by reference.

In one aspect of the present invention is provided a method for fluoride treatment of a ceramic surface (e.g., a surface of a bulk ceramic such as a ceramic medical implant or a surface of a ceramic particle) by exposing the ceramic surface to a fluorine-containing reagent. In some embodiments, such treatment changes the chemical makeup of the surface of the ceramic. In certain embodiments, the fluoride treatment of the surface provides a surface that is more reactive than the untreated surface. Thus, this method may provide a surface that is more susceptible to further functionalization with various reagents. Although not bound by any theory of operation, it is believed that the fluorination processes of the invention result in fluorine replacing oxygen in the oxide lattice near the surface of the ceramic, thus creating a metastable, partially covalent, partially ionic bond. This bond may be capable of reacting with various reagents, including, but not limited to, conventional silane coupling agents. In certain embodiments this bond may be capable of directly reacting with conventional dental cements (e.g., resins) without the need for an intervening silane coupling agent.

In certain embodiments, the fluoride treatment of the ceramic surface as disclosed herein provides a surface with higher wettability than the untreated surface. Interestingly, fluoride treatment is typically conducted to make a surface more hydrophobic. However, as disclosed herein, in certain embodiments, fluoride treatment may provide a surface characterized by a higher wettability (i.e., greater hydrophilicity) than the untreated surface. See, for example, FIGS. 3(B) and 3(C). In some embodiments, this higher wettability may be quantified by a smaller contact angle than that observed prior to fluoride treatment. For example, in certain embodiments, the contact angle may be less than about 50°, less than about 25°, less than about 10°, or less than about 8°. In certain embodiments, the contact angle may be between about 5° and about 20°, or between about 5° and about 10°. The contact angle may be determined with any method typically used for this purpose. For example, in some specific embodiments, a KRUSS EasyDrop Standard instrument is used. In certain embodiments, ASTM D7490 (2008) is used to determine wettability.

In some embodiments, the fluoride treatment is accomplished by plasma treatment. Plasma treatment, as used herein, generally comprises exposing the ceramic material to a fluoride ion source in plasma form. Typically, such a method involves generating a plasma field in an electrically charged atmosphere, e.g., in a plasma chamber. A traditional plasma setup comprises a chamber in which the sample to be treated may be contained, which is capable of receiving a selected gas flow; a vacuum source; and a power supply. However, any setup capable of providing fluoride ions in plasma form may be used according to the presently disclosed method. For example, in one specific embodiment, a planar inductively coupled RF Plasma tool from Oxford Instruments may be used.

In some embodiments, exposure to plasma treatment allows low molecular weight materials such as water and adsorbed gases to be removed from the surface to expose a clean, fresh surface. Some percentage of the reactive components in the plasma have sufficient energy to bond to the freshly exposed surface, changing the chemistry of the surface and imparting the desired functionalities. In certain embodiments, the reactive components comprise fluoride ions.

The composition of the plasma may be varied. The fluoride ion source may be any fluorine-containing reagent in gas or liquid form that, in plasma form, can provide fluoride ions. For example, in some embodiments, the fluoride ion source comprises sulfur hexafluoride ($SF_6$). In other embodiments, the fluoride ion source comprises $CF_4$, $C_4F_8$, $C_5F_8$ (octafluorocyclopentene), $C_4F_6$ (hexafluoro-1,3-butadiene), $NF_3$, $SiF_4$, or combinations thereof. In some embodiments, the fluoride ion source comprises a chlorofluorocarbon (CFC). A CFC is any compound having chlorine, fluorine, and carbon atoms. For example, when derived from methane and ethane, CFCs have the formulae $CCl_mF_{4-m}$ and $C_2Cl_mF_{6-m}$ respectively, where m is nonzero. In some embodiments, the fluoride ion source comprises a hydrofluorocarbon (HFC). An HFC is any compound having hydrogen, fluorine, and carbon atoms. For example, when derived from methane, ethane, propane, and butane, these compounds have the formulae $CF_mH_{4-m}$, $C_2F_mH_{6-m}$, $C_3F_mH_{8-m}$, and $C_4F_mH_{10-m}$ respectively, where m is nonzero. In some embodiments, the fluoride ion source comprises a hydrochlorofluorocarbon (HCFC). An HCFC is any compound having hydrogen, chlorine, fluorine, and carbon atoms. For example, when derived from methane and ethane, HCFCs have the formulae $CCl_{m-}F_nH_{4-m-n}$, and $C_2Cl_xF_yH_{6-x-y}$ respectively, where m, n, x, and y are nonzero. In some embodiments, the fluoride ion source comprises a bromochlorofluorocarbon or bromofluorocarbon. These compounds are similar to HCFCs and CFCs, respectively, with appropriate replacements with bromine atoms.

This list of fluoride ion source reagents is not intended to be limiting. Other liquid or gaseous reagents capable of providing fluoride ions in plasma form are also contemplated as being useful according to the presently described method.

The parameters within the plasma chamber may vary. For example, the power source used to generate the plasma may be of any type, including but not limited to, DC, RF and microwave. The electrode configuration used to generate the plasma may also be varied. The degree of ionization within the plasma may be varied, including fully ionized, partially ionized, or weakly ionized. The pressure at which the system operates may be varied, including but not limited to, within the range of vacuum pressure (<10 mTorr or 1 Pa) to moderate pressure (~1 Torr or 100 Pa) to atmospheric pressure (760 Torr or 100 kPa). The temperature relationships within the plasma may also be varied, ranging from a thermal plasma ($T_e=T_{ion}=T_{gas}$), where e=electron, to a non-thermal or "cold" plasma ($T_e>>T_{ion}=T_{gas}$). The plasma may be magnetized, partially magnetized, or non-magnetized.

The period of time for which the ceramic surface is exposed to the plasma may vary. In certain embodiments, the exposure time ranges from about 1 second to about 100 minutes, and preferably from about 20 seconds to about 2 minutes. The plasma power may vary. In certain embodiments, the plasma power is within the range of about 50 to about 1000 W, and preferably within the range of about 600 to about 800 W. One specific set of parameters that may be used according to the present invention includes a planar, inductively coupled 13.56 MHz radio-frequency plasma reactor at 800 W with a dc bias of ~300V for about 2 minutes.

The ceramic surface may be untreated or may be treated in some way prior to being subjected to the fluoride treatment. For example, the surface may be roughened, for example, by polishing with polishing paper, and/or air-abrading with alumina or other types of particles. The degree of surface roughening required may vary, depending on the particular application. The ceramic surface may be treated with oxygen-containing plasma prior to the disclosed treatment method, for example, to eliminate organic contaminants.

Although the fluoride treatment method described above relates to plasma treatment, other means for the fluoride treatment of a ceramic surface are contemplated and encompassed within the present invention. In some embodiments, any liquid reagent capable of generating fluoride ions may be used in combination with a physical or chemical treatment capable of providing sufficient energy to facilitate reaction between the surface and the fluoride ions in the absence of plasma generation. In this manner, treatment of the ceramic surface could occur using a slurry or gel comprising the fluoride ion source in combination with a second component that provides physical roughening or chemical etching of the surface. The role of the second component is to facilitate scission of bonds in the metal oxide structure, resulting in enhanced reactivity of the metal oxide surface with the fluorine-containing reagent. In some embodiments, the fluoride ion source and the second component are provided within the same composition. In some embodiments, the fluoride ion source and the second component are provided within separate compositions. In some embodiments, the fluoride ion source and the second component are applied to the ceramic material together. In other embodiments, the fluoride ion source and the second component are applied as separate treatments (e.g., a physical or chemical treatment is first applied to the ceramic, followed by treatment with a composition comprising a fluoride ion source).

For example, in certain embodiments, the ceramic surface is treated with a reactive chemical etchant in combination with a fluoride-generating reagent. In some embodiments, the reactive etchant and/or fluoride-generating reagent may be contained within a solution or slurry, including, but not limited to, an aqueous solution. The reactive etchant may be any reagent that etches the surface of the ceramic material. For example, the etchant may comprise sulfuric acid ($H_2SO_4$), hydrofluoric acid (HF), hydrochloric acid (HCl), hydrogen peroxide ($H_2O_2$), phosphoric acid ($H_3PO_4$), ferric chloride (FeCl), nitric acid ($HNO_3$), or a combination thereof. For example, in certain embodiments, the etchant may comprise a combination of HF and $HNO_3$ or $H_2SO_4$ and $HNO_3$. Obviously, the composition of the ceramic will govern which reagents will etch the surface of the ceramic material. Other reagents that may etch the ceramic are also encompassed within the class of reagents that may be used for this purpose.

In certain embodiments, the ceramic is treated with a physical abrasive and reacted with a fluoride-containing reagent. In some embodiments, the physical abrasive may be contained within a gel-type composition. The physical abrasive may be any material that can roughen the surface of the medical implant. For example, the physical abrasive may be pumice, diamond grit, alumina or zirconia particles, and/or silicon carbide. Other materials that may physically roughen the ceramic surface are also encompassed within the class of physical abrasives that may be used for this purpose. In some embodiments, a combination of chemical etchant and mechanical abrasive may be used.

In one embodiment of the present invention, the fluorination treatment described herein is followed by a molecular vapor deposition (MVD) process to apply a silicon oxide coating to the surface. For a more detailed description of such a process, see, for example, United States Application Publication No. 2012/0034572 to Piascik et al., which is incorporated herein by reference. In such embodiments, the reagents utilized in the molecular vapor deposition include one or more silicon-based precursors. Briefly, a silicon-based precursor and optionally one or more additional reagents react with the surface, forming active hydroxyl groups on the surface, subsequently forming a silicon oxide layer on the substrate surface. The silicon-based precursor may be any silicon-containing species, including mono-, di-, and tri-silanes and siloxanes that can be vaporized. The silicon-based precursors include, but are not limited to, tetrachlorosilane ($SiCl_4$), tetrafluorosilane ($SiF_4$), tetrabromosilane ($SiBr_4$), trichlorosilane ($HSiCl_3$), trifluorosilane ($HSiF_3$), tribromosilane ($HSiBr_3$), hexachlorodisilane ($Si_2Cl_6$), hexachlorodisiloxane ($Si_2Cl_6O$), and combinations thereof. In one embodiment, the silicon-based precursor is tetrachlorosilane and an additional reagent is water vapor. In some embodiments, multiple layers are deposited on the surface via this method. The deposited silicon oxide layer may be continuous or discontinuous on the surface.

The surface fluorination process of the present invention, when used prior to and in combination with the MVD process described above, may lead to better performance of the surface as compared to a surface that may be obtained using MVD on a non-fluoride treated surface. In some aspects, the fluorination treatment may provide a more reactive surface, leading to a more effective silicon oxide-coated surface following MVD, such as by improving adhesion of the silicon oxide layer or improving surface coverage of the silicon oxide layer. A silicon oxide coating may be desirable in certain applications, including but not limited to, applications involving cell attachment and/or integration.

The methods described herein may be applicable to various materials which may have available hydroxyl groups on their surfaces, but preferably is applicable to zirconia or alumina. In some embodiments, the ceramic may comprise titania, or chromium oxide. In certain specific embodiments, the ceramic comprises yttria-stabilized zirconia (YSZ). The ceramic may have an activated surface resulting from treatment with a fluoride-containing reagent as described above. In certain embodiments, the activated ceramic surface comprises a fluorinated metal oxide. Although not wishing to be bound by theory, it is thought that the activated surface comprises a metal oxyfluoride (e.g., zirconium oxyfluoride ($ZrO_xF_y$)). The activated surface may be continuous or discontinuous. For example, in certain embodiments, there may be "islands" of fluoride phases on a surface comprising an oxyfluoride phase. For example, the fluorinated metal oxide surface may comprise a mixture of metal oxyfluoride and metal fluoride phases. FIG. 1 shows an example of an activated surface having oxyfluoride and fluoride phases.

The thickness of the activated surface may vary. For example, in certain embodiments, the activated surface has a thickness of from about 0.5 nm to about 5 nm, preferably from about 1 nm to about 5 nm, and more preferably from about 1 nm to about 3 nm. In certain aspects, this means that the medical implant comprises a fluorinated metal oxide surface having a thickness within these ranges.

In some embodiments, a fluoride-treated ceramic surface may alternatively be directly functionalized with a cement (e.g., a resin), giving a ceramic surface coated with cement. In one embodiment, the cement is covalently bonded to the fluoride-treated surface. In certain embodiments, the cement is bonded more strongly to the fluoride-treated surface than cement bonded to an untreated medical implant.

V. Examples

Example 1

Zirconia Surface Modified by Fluorination, Bonded to Organosilane and then to Cement Materials and Methods Blocks of pre-sintered zirconia (ZirCAD®, Ivoclar-Vivadent, Schaan, Liechtenstein) measuring 14×12×20 mm were obtained from the manufacturer and sectioned into 2 mm plates. Composite cylinders (Filtek™ Supreme, 3M-ESPET™, St. Paul, Minn.) were fabricated by condensing the material into a Teflon mold (2 mm diameter×3 mm height) and UV light-activated for 40 seconds at 500 mW/cm². Surfaces of each material were highly polished through 50 μm diamond grit polishing paper to ensure starting surface roughness. After polishing, select surfaces were air-abraded (50 μM alumina abrasive, 0.29 MPa, 20 sec) prior to chemical surface treatments and/or bonding procedures. Abraded specimens were rinsed with iso-propanol and submersed in DI ultrasonic bath for 5 minutes.

Zirconia specimens were fluorinated in a planar, inductively coupled 13.56 MHz plasma reactor at 800 W with a dc bias of −300V. A continuous flow source gas of $SF_6$ at 25 sccm was used to maintain a pressure of 35 mT for 2 min. X-ray photoelectron spectroscopy (XPS) was used to evaluate surface chemistry and stoichiometry of the conversion layer. A Kratos Analytical Axis Ultra XPS system with a monochromatic Al kα source operated at 15 kV and pass energy of 20 eV was used to obtain Zr 3d core level spectra. The spectra was then deconvoluted using CasaXPS™ software employing a Shirley background subtraction and mixed Gaussian-Lorentzian (G-L) peaks associated with the oxide and oxyfluoride components. The spectra were referenced to the Zr $3d_{5/2}$ peak at 182.2 eV for $ZrO_2$.

Below are the seven groups (n=10) from which shear bond specimens were fabricated, with variations for each surface treatment. All shear bond specimens were prepared using the same bonding procedure. Zirconia surfaces were modified (see below for modification techniques) and treated with an organosilane (Monobond-S, Ivoclar-Vivadent, Schaan, Liechtenstein) prior to resin cement bonding. Composite cylinders were coated with resin cement (Rely-X™ Unicem, 3M-ESPE™, St. Paul, Minn.), placed on the zirconia surface, and UV-light cured under a defined load (5 N):

- Group 1 and 2: (control): (1) Polished, untreated surface and (2) roughened, untreated surface.
- Group 3 and 4: Surfaces were polished (3) or roughened (4) and were modified with a 3 nm $Si_xO_y$ layer (this procedure is described in detail in J. R. Piascik et al., Surface Modification for Enhanced Silanation of Zirconia Ceramics, Dental Mater. 25: 1116-1121 (2009), incorporated herein by reference in its entirety). Group 5: Zirconia surfaces were silica-coated using 30 μm alumina particles modified with salicylic acid (CoJet®, 3M-ESPET™, St. Paul, Minn.—0.28 MPa, 5-10 mm working distance, 15 sec).
- Group 6 and 7: Zirconia surfaces were polished (6) or roughened (7) and were exposed to the fluorination process described above.

Shear bond test specimens were stored in DI water at 37° C. for a period of 24 hours prior to testing. Specimens were then fixed to a custom vise fixture to ensure vertical compliance. All specimens were subjected to a force at a crosshead speed of 0.5 mm/min in an electro-mechanical testing device (Instron Corp., Norwood, Mass.). Shear bond strengths were calculated by dividing peak load by the cross-sectional area of the composite cylinder. Single-factor analysis of variance (ANOVA) at a 5% confidence level was performed for the bonding strength data. Optical microscopy and scanning electron microscopy (SEM) were used to evaluate and quantify failure surfaces.

Results

The mean values and standard deviations of the shear bond strength mechanical testing are graphically shown in FIG. 4. In this figure, shear bond stress values for all groups tested are provided, with values plotted with standard deviation error bars (brackets { } denotes effect of fluorination process on roughened and polished surfaces respectively). It should be noted that the fluorinated (polished) group was statistically the same as a clinically accepted tribochemical treatment. Single-factor ANOVA analysis revealed a significant difference in mean shear bond strengths. As expected, the untreated polished zirconia specimens were shown to have the lowest shear strength. The fluorinated zirconia specimens (both rough and polished) displayed the highest shear bond strengths as compared to other commercially available treatments. Furthermore, the fluorinated polished specimens were statistically similar to those that were mechanically roughened using a commercial tribochemical approach.

Figure 5:
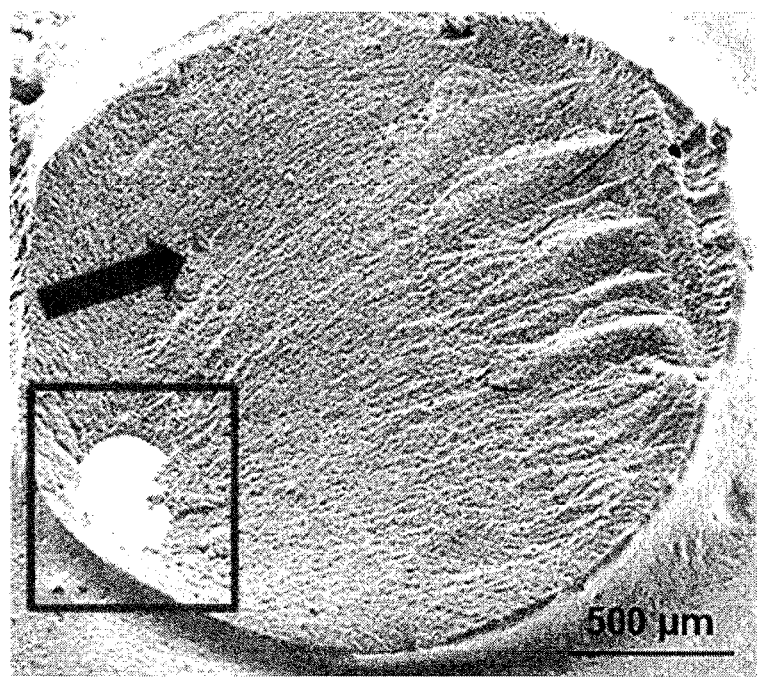
Figure 5:
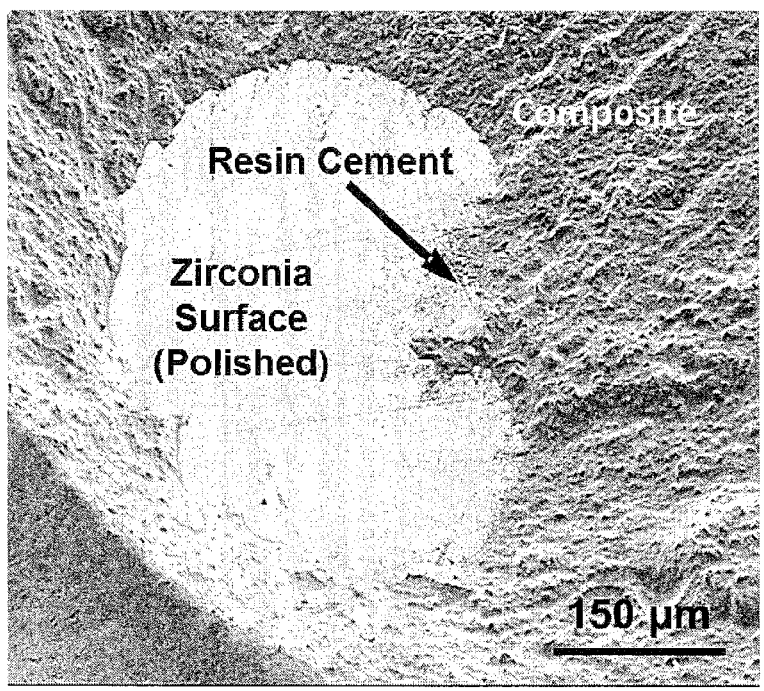

Table 1, below, displays the shear bond values with standard deviation and percent failure mode. Optical and SEM analyses revealed a higher percentage of adhesive/cohesive failures for the fluorinated group of specimens. This type of failure indicates high bond strength between the two substrates due to the nature of shear bond testing. The force placed on the cylinder during testing creates a dual-mode of tensile and compressive stresses at the bonding interface, thus creating a failure surface that reveals an area of adhesive failure (noted by exposure of either zirconia surface and/or resin cement) along with composite still adhered to the zirconia surface. There are several factors that can contribute to variations in shear bond load values. Larger bonding areas can induce processing flaws which can promote premature bond failure, and variation in bonded composite can generate disparities in shear bond values. FIG. 5 shows representative SEM micrograph images of a fluorinated (polished) specimen with adhesive/cohesive failure. FIG. 5(A) is a low magnification where the arrow shows shear force direction and FIG. 5(B) is a high magnification area within the box. The white areas are the zirconia surface and small dark regions shows areas of resin cement and composite.

TABLE 1

Shear bond stress (MPa) with standard deviation of the different test groups.

| Sample Group (with surface finish) | Shear Bond Stress (MPa) | Standard Deviation | A (%) | A/C (%) |
|---|---|---|---|---|
| Fluorination (rough)[a] | 32.67 | 6.43 | 10 | 90 |
| Fluorination (polished)[b] | 26.32 | 6.35 | 30 | 70 |
| Co-Jet ™ (rough)[b] | 24.44 | 4.94 | 30 | 70 |
| 3 nm $Si_xO_y$ (rough)[b] | 22.88 | 4.69 | 40 | 60 |
| 3 nm $Si_xO_y$ (polished)[c] | 18.58 | 2.79 | 80 | 20 |
| Untreated (rough)[c] | 15.58 | 1.98 | 90 | 10 |
| Untreated (polished)[d] | 10.08 | 3.76 | 100 | 0 |

The A column shows the percent of samples displaying adhesive failure; the A/C column shows the percent of samples displaying a mixed mode of adhesive and cohesive failure. The superscripted letters in the first column represent the same statistical grouping (i.e., items with the same letter are statistically the same).

Figure 6:
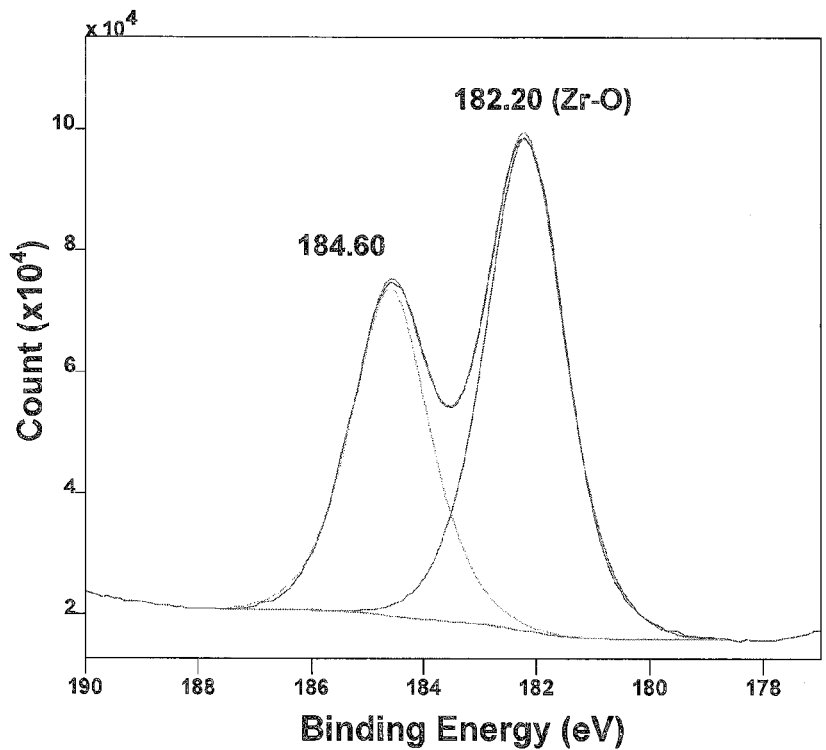
Figure 6:
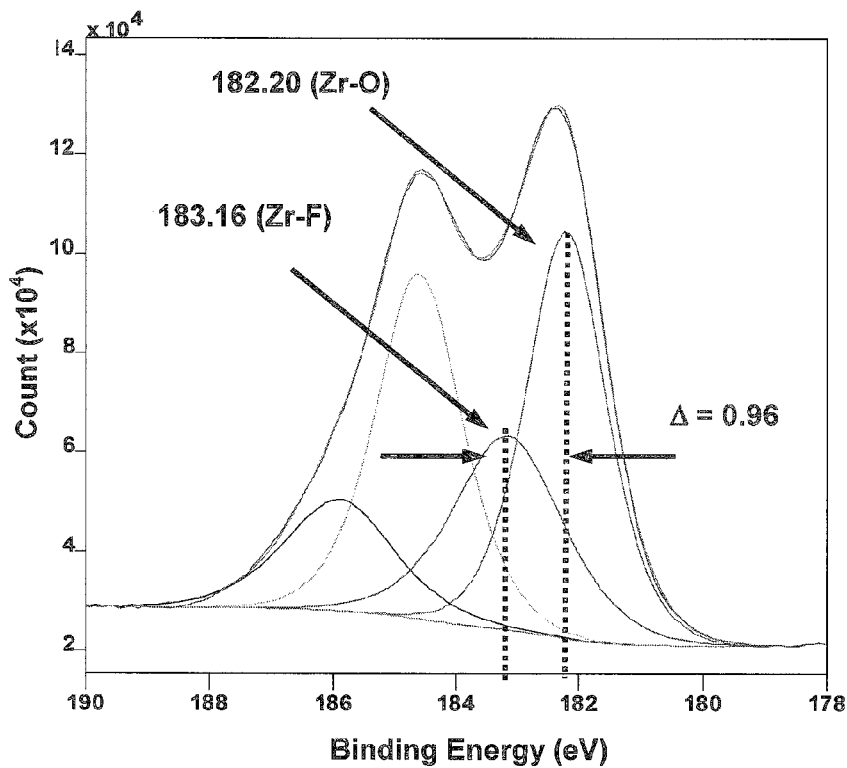

XPS survey scans of an untreated specimen were used to establish a baseline of near surface chemistry for comparison to fluorination results. Survey scans of the fluorinated specimens revealed the presence of fluorine (1s) accompanied by a reduction in oxygen (1s). XPS Core scans of the $Zr^+$ 3d doublet as shown in FIG. 6 were performed on an untreated zirconia specimen (FIG. 6(A)) and a fluorinated zirconia specimen (FIG. 6(B)). These scans highlighted an interesting phenomenon: In addition to the Zr—O doublet at 182.20 eV, there was a component of the signal shifted to higher binding energy, 183.16 eV (see FIG. 6(b)). This increase in binding energy suggests a structure that is more ionic (and more reactive) and characteristic of zirconium oxyfluoride ($ZrO_xF_y$).

Discussion

Based on an article by Panton and Brow (*J. Am. Ceram. Soc.* 1988; 71(7): 577-581), incorporated herein by reference in its entirety, we can approximate the zirconium oxyfluoride stoichiometry for the above specimen as, $ZrO_3F_4$ (see FIG. 7). FIG. 7 shows the relationship between Zr 3d binding energy and the Pauling charge on $Zr^+$-cation. Added data points are the Zr 3d binding energies measured via XPS from an (a) untreated and (b) fluorinated specimen, respectively.

To determine depth and chemical bonding modification to the structure, angle resolved and Ar-sputter XPS were performed. Based on these experiments and grain size analysis of the zirconia, it is proposed that the fluorination treatment converts the surface of $ZrO_2$ to a zirconium oxyfluoride with an average thickness of 20-30 Å and non-uniformly distributed across the surface. See FIG. 2 for a schematic representation of the sintered zirconia and the subsequent oxyfluoride conversion. Fluorinated plasma is applied to the zirconia surface, converting the top 1-3 nm into a surface comprising zirconium oxyfluoride ($ZrO_xF_y$). The oxyfluoride surface can react with organosilanes, enabling silicon attachment to the surface.

In order to test adhesion strength of dental materials, simple shear bond or microtensile mechanical testing is often used. Both, however, have drawbacks when attempting to evaluate the true bond strength. It has been reported that microtensile tests are better at eliminating any macro-sized flaws produced when fabricating specimens, thus providing a closer approximation to the ideal strength. Unfortunately these samples are very time consuming to produce and simply cutting the specimens into final form may introduce stresses from the cutting tool that cannot be quantified. Shear bond testing, however can be used as general baseline and a clinically more relevant bonding area. The test does introduce a multi-mode stress profile: the bonding area will experience tensile stresses at the top (initial point of force) and compressive forces near the center and bottom of the bonding interface.

In order to establish an understanding of how surface preparation and bonding procedures are critical to bond strengths, both polished and physically abraded surfaces were evaluated. Relatively low bond strengths (ranging from 10 to 15.6 MPa for polished and roughened, respectively) are reported here for specimens bonded with a phosphoric acid modified methacrylate monomer cement. These results are not unexpected since other reports have shown that unmodified surfaces display low bond strengths and eventually lead to adhesive failure. The lack of chemical bonding between the two materials is the overriding contributing factor for low bond strengths. This had led to research efforts that seek chemical and mechanical techniques that improve adhesion.

Interestingly, a fluorinated surface, either polished or roughened, displayed the highest shear bond strengths (26.3 and 32.7 MPa, respectively). It is noted that 70% of the fluorinated polished specimens exhibited adhesive/cohesive behavior, whereas 0% of the untreated polished specimens displayed this characteristic. These data show that the fluorinated treatment on roughened zirconia displayed the highest shear bond strength and even more promising is that the fluorinated treatment on polished zirconia was statistically the same as (or higher than) other clinically accepted methods. This finding suggests that the fluorination treatment could be used on as-received substrates, where roughening or other surface modification techniques are neither possible nor desired. Although not wishing to be bound by theory, it is hypothesized that the presence of an oxyfluoride phase on the zirconium oxide surface may increase its reactivity with silanes by facilitating Zr-hydroxylation via H—F extraction in the presence of water. Oxyfluorides have been shown to be more reactive in aqueous environments.

Conclusion

Simple shear bond mechanical tests demonstrated that a fluorination pre-treatment is a viable method to chemically modify zirconia to produce a reactive surface for adhesive bonding. By using XPS analysis, it was determined that this novel treatment process created an oxyfluoride conversion layer that is receptive to organosilane chemical attachment.

Example 2

Yttria-stabilized Zirconia Modified by Fluorination and Bonded Directly to Cement Presented in this example is an in-depth analyses of the fluorination process on YSZ surfaces and the resulting phases that form in the thin conversion layer (see, for example, FIG. 1). The motivation for this work was to create a reactive surface that would allow for chemical interaction with acrylate based resin cement without the use of silanes or primers. Simple shear bond tests were employed to measure adhesion on as-received (non-roughened) and roughened specimens and compared to alternative pretreatment techniques.

Materials and Methods

Pre-sintered plates and cylinders of YSZ shear bond specimens (LAVA, 3M ESPE AG; Seefeld, Germany) were obtained from the manufacturer. As-received surfaces (both plates and cylinders) were air-abraded (50 μm alumina abrasive, 0.29 MPa, 20 sec) prior to surface modification treatments and rinsed with isopropanol, then ultrasonically cleaned in DI for 5 minutes.

Bonding surfaces were then fluorinated in a planar, inductively coupled 13.56 MHz radio-frequency plasma reactor at 800 W with a dc bias of ~300V. Water cooling of the substrate platform ensured process temperatures did not exceed 100° C. A continuous flow source gas of $SF_6$ at 25 sccm was used to maintain a pressure of 35 mT at varying times of 20 sec, 2 min, and 5 min. For each process time, YSZ cylinders (n=12) were coated with resin cement (Rely-X Unicem, 3M-ESPE, St. Paul, Minn.) per manufacturer's instructions, placed directly on the plate surface and UV-light-curing was performed under a defined load (5 N). Untreated specimens were used as a control for the shear bond testing. Shear bond test specimens were stored in DI water at 37° C. for a period of 24 hours prior to testing, then fixed to a custom fixture to ensure vertical compliance. Specimens were subjected to a force at a crosshead speed of 0.5 mm/min in an electro-mechanical testing system (Instron Corp, Norwood, Mass.). Shear bond strengths were calculated by dividing peak load by the cross-sectional area of the composite cylinder. Single-factor analysis of variance (ANOVA) at a 5% confidence level was performed for the bonding strength data for statistical similarities. Scanning electron and optical microscopy was used to evaluate bonding surfaces.

X-ray photoelectron spectroscopy (XPS) was used to evaluate surface chemistry and stoichiometry of the conversion layer. A Kratos Analytical Axis Ultra XPS system (Manchester, UK) with a monochromatic Al kα source operated at 15 kV and pass energy of 20 eV was used to obtain surface survey, Zr and Y 3d core level spectra and deconvoluted using CasaXPS™ software. A Shirley background subtraction and mixed Gaussian-Lorentzian (G-L) peaks associated with oxide, oxyfluoride, and fluoride components were deconvolved to reveal near surface phases operative in adhesive bonding chemistry. Additionally, as-received YSZ plates were exposed to the above mentioned fluorination times. X-ray diffraction (XRD) (Philips X'Pert PRO MRD HR, PANalytical Inc., Westborough Mass.) was used to quantify potential phase transformation post exposure.

Results

Shear bond values of all groups tested are shown graphically in FIG. 8 with standard error bars. The shear bond data show an increase in bond strength with treatment time. As expected the as-received (polished) specimens displayed lowest bond strengths, indicating no chemical attachment between YSZ surfaces and resin cement. As-received, untreated, and 2 min fluorinated specimens were tested to evaluate potential non-roughening effects on adhesive strength. It should be noted that the 2 min as-received (polished) group was statistically higher as compared to the clinically accepted method (roughened +resin cement). The 5 and 2 minute treated specimens were shown to have the highest bond strengths, 33.7 and 31.5 MPa, respectively. Table 2 displays shear bond strength values with standard deviations. The superscripted letters in the first column represent the same statistical grouping (i.e., items with the same letter are statistically the same).

TABLE 2

Shear bond stress (MPa) with standard deviation of the different test groups

| Sample Group (w/surface treatment) | Shear Bond Stress (MPa) | Standard Deviation (%) |
|---|---|---|
| 5 minute treatment (rough)[a] | 33.7 | 6.4 |
| 2 minute treatment (rough)[a] | 31.5 | 6.9 |
| 2 minute treatment (as-received)[b] | 26.7 | 4.9 |
| 20 second treatment (rough)[c] | 22.9 | 4.7 |
| Untreated (rough)[c] | 18.6 | 2.8 |
| Untreated (as-received)[d] | 9.2 | 6.2 |

Evaluation of failure modes differ from conventional shear bond analysis due to the fact that shear bond specimen components were the same material. Typically, when testing two dissimilar materials, with distinct differences in material properties, it would be common to see either an adhesive failure, cohesive, or mixed mode (failure displaying both adhesive and cohesive properties). Here, all failures are quantified as adhesive failures (see FIG. 9), due to the fact that resin cement is the weak link in the bonding of the two materials. All failure surfaces, with the exception of the untreated groups, displayed a percentage of resin cement bonded to both plate and cylinder. Based on the shear bond values, there are two scenarios that can be considered for the increase in bond strength: (1) an increase in surface area due to particle air-abrasion as shown in as-received compared to roughened groups and/or (2) the increase in surface reactivity with the resin cement facilitating increase in covalent bonding between the substrate and cement.

X-ray photoelectron spectroscopy (XPS) analysis was performed on both as-received (non-roughened) and fluorinated YSZ plates, and used to evaluate the chemistry and stoichiometry of the conversion layer. All spectra were referenced to the Zr $3d_{5/2}$ peak at 182.2 eV for $ZrO_2$. FIGS. 10(A) and 10(B) show Zr and Y 3d spectra, respectively, as a function of fluorination time (referenced to unprocessed YSZ). The deconvolved spectra reveal formation of Zr-oxyfluoride, Zr-fluoride, and Y-fluoride for process durations of 20 sec to 5 min. The Zr 3d spectra were characterized by similar proportional amounts of oxyfluoride and fluoride phases. The near surface yttrium levels, however, increased considerably with fluorination time, and by as much as 54% for the 5 min specimen (relative to the unprocessed YSZ). This result is noteworthy and will be discussed in greater detail in the following sections. Furthermore, yttrium fluoride (YF$_x$) was observed, and increased with longer processing, and in contrast to the zirconium phases, no evidence of Y-oxyfluoride phases were detected. The collective data indicate a broad processing window for producing a reactive surface conversion layer.

XPS revealed an increase in both fluoride and oxyfluoride compounds on the surface of treated specimens. Interestingly, shear bond strength and change in % Y surface concentration trend in the same direction as a function of treatment time (FIG. 3(A), showing shear bond strength values with standard error bars). Data showed that as surface treatment time increased, so did adhesion strength and % Y concentration. The increase in bond strength would indicate that the surface is becoming populated with a higher concentration of reactive sites leading to an increase in potential covalent bonding with the resin cement. Simple contact angle measurements, sessile drop method, were performed to evaluate the wettability of a planar untreated and a 2 min fluorinated specimen. The contact angle for the untreated specimen is 58° (FIG. 3(C)) and a specimen after a 2 min treatment is 6° (FIG. 3(B)). This change to a lower contact angle would indicate a surface that is highly hydrophilic, increasing its wettability and surface reactivity.

X-ray diffraction was performed on the above mentioned specimens to evaluate crystal structure and potential phase transformation (tetragonal to monoclinic) based on treatment time. FIG. 11(A) displays diffraction 2-theta scans revealing that YSZ untreated and treated specimens consist of purely tetragonal phases. No monoclinic phases were detected within the resolution of the diffractometer, suggesting that the fluorination plasma treatment used in this study will not elicit a tetragonal to monoclinic phase transformation. Based on the fact that this was a surface treatment, limited to the top 2-5 nm, glancing angle) (~2° diffraction was also performed (FIG. 11(B)). These results mirrored the bulk diffraction analysis, indicating that the crystal structure, even near the surface, is tetragonal and apparently unchanged from that of the as-received bulk material.

Discussion

This study evaluated an alternative method to increase the wettability and chemical reactivity of YSZ surfaces using a novel fluorination technique. It has been well established that application of silane primers to silicon-based materials show increased adhesion with resin cements and bond to surface hydroxyl groups of polar surfaces. However, these techniques used by clinicians are not suitable for zirconia-based materials, which are classified as inert or non-reactive.

As controls for the present study, untreated polished and roughened specimens were evaluated for adhesion. The polished specimens displayed the lowest strength (9.2 MPa), as expected and in agreement with the previous example. Surface roughening increased the strength (18.6 MPa); however, this is attributed primarily to an increase in surface area and not to chemical attachment with the resin cement. As shown in FIG. 3(A), an increase in fluorination time resulted in increasing shear bond strength, suggesting that there may be further optimization of this treatment that could potentially exhibit higher bond strengths, a more robust interface, or some combination of the two. It is also noted that there is a saturation in the trend and more detailed chemical analyses are currently underway to understand the nature of this trend. As shown earlier, this increase in bond strength suggests that the enhanced surface reactivity may be directly correlated to the conversion of the Y—ZrO$_2$ (YSZ) structure to three distinct phases of Zr-oxyfluoride, Zr-fluoride, and Y-fluoride.

To help explain the reactivity of fluorinated zirconia and yttria compounds, we recalled an earlier study by Pantano and Brow (J. Am. Ceram. Soc. 1988; 71(7): 577-581), which investigated the surface reactivity associated with hydrolysis of fluorizirconate glasses. They used XPS to characterize the various stoichiometries of zirconium oxyfluorides (ZrO$_x$F$_y$) by plotting the binding energy for the Zr 3d photoelectron as a function of the Pauling charge on the Zr$^+$-ion. It was reported that subsequent Zr-oxyfluoride phases produced during hydrolytic exposure are seven-fold coordinate species. The seven-fold coordination is based on one fluorine loss for each oxygen incorporated into the oxyfluoride phase. A detailed surface analytical study of the plasma fluorination of YSZ confirmed that the phases present at the surface are of 7-fold symmetry and propose that the Zr-oxyfluoride stoichiometry formed during this plasma conversion process is ZrO$_2$F$_5$. Furthermore, in comparing the relative Yttrium to Zirconium levels as a function of fluorination time (FIG. 12) and then assigning their bonding components via XPS deconvolution, we discover that there is an increase in total Yttrium concentration at the surface, and that increase is primarily associated with the formation of yttrium fluoride (YF$_3$).

Low temperature (<100° C.) diffusion of Y in YSZ has not been reported; however, the data in FIG. 12 show a greater than 50% increase in Y/Zr ratio within the top 3-5 nm after 20 min. of plasma fluorination. The XPS deconvolution attributed this increase to YF$_3$ formation. It is possible that this increase in Y-surface concentration could be the result of grain-boundary depletion and surface diffusion, driven by the strong chemical potential formed by the presence of fluorine on the surface. In addition to forming a Zr-oxyfluoride phase, the majority of the original Y—ZrO$_2$ and increased yttrium appears to be converting to Y-fluoride. One concern was that significant depletion of Y from the sub-surface YSZ lattice might drive the metastable tetragonal lattice towards the room temperature monoclinic phase. However, the surface conversion layer is only 3-5 nm thick and data from glancing angle x-ray diffraction (FIG. 11(B)) detect only tetragonal phases. The source of this increased Y/Zr ratio in the near surface region and the role it plays in increasing surface reactivity is the subject of ongoing research. Although not bound by any particular theory of operation, it is believed that the zirconium-oxyfluoride phase is the dominant contributor to increased bond-strength for YSZ surfaces. Future work will study the chemical bonding between this surface and various acrylate compounds and the roles that conversion layer thickness and stoichiometry play on resulting bond strength and phase stability.

Conclusion

This study analyzed YSZ to YSZ adhesion using a common acrylate-based resin and mechanical data revealed an increase in adhesion strength as a function of fluorination exposure time. This modification process did not utilize an organosilane coupler or metal primer to increase chemical bonding between the substrates, potentially eliminating the need for silanation. It is hypothesized that these results can be applied to other bonding scenarios involving YSZ (i.e., composites, titanium, porcelain, etc.). XPS analysis revealed an increase in Y-fluoride, as well as Zr-oxyfluoride and Zr-fluoride with treatment time.

That which is claimed:

1. A dental composite material comprising a polymerizable resin and a particulate filler dispersed therein, wherein the filler comprises ceramic particles having a fluorinated metal oxide surface, wherein at least a portion of the ceramic particles comprise an antimicrobial agent attached thereto, the antimicrobial agent selected from the group consisting of silver acetate, silver benzoate, silver carbonate, silver ionate, silver iodide, silver lactate, silver laureate, silver nitrate, silver oxide, silver palmitate, silver protein, silver sulfadiazine, calcium oxide, calcium hydroxide, magnesium oxide, magnesium hydroxide, barium oxide, barium hydroxide, strontium oxide, strontium hydroxide alkali, chlorhexidine; 5-chloro-2(2-4-dichlorophenoxy)phenol), polyhexamethylenebiguanide hydrochloride (PHMB), doxycycline, metronidazole, thymol, encalypol, methyl salicylate, 4'-sulfamoylsulfanilanilide, 3-amino-6-(2-(5-nitro-2-furyl)vinyl)pyridiazine, transpseudomonic acid, xanthomycin, alpha-amino-p-toluene sulfonamide, alpha-azido benzyl penicillin, penicillin O, penicillin N, monopropionyl erthromycin, erythromycin 9(O-((2-methoxyethoxy)methyl) oxime; 1,1'-hexamethlene bis(5-(p-chlorophenyl)biguanide), cetyl pyridinium chloride; benzalkonium chloride, cetyl pyridinium bromide, 2,4,4'-trichloro-2'-hydroxy-diphenyl ether, antimicrobial peptides, and combinations thereof.

2. The dental composite material of claim 1, wherein the fluorinated metal oxide surface comprises a mixture of metal oxyfluoride and metal fluoride phases.

3. The dental composite material of claim 1, wherein the ceramic particles comprise a material selected from the group consisting of zirconia, alumina, titania, and chromium-oxide-based materials.

4. The dental composite material of claim 1, wherein at least a portion of the ceramic particles further comprise a silane coupling agent overlying the fluorinated metal oxide surface.

5. The dental composite material of claim 4, wherein the silane coupling agent is selected from the group consisting of 3-methacryloyloxypropyltrimethoxysilane, 3-trimethoxysilylpropylmethacrylate, 3-acryloyloxypropyltrimethoxysilane, 3-isocyanatopropyltriethoxysilane, N-[3-(trimethoxysilyl)propylethylenediamine],3-mercaptopropyltrimethoxysilane, bis[3-(triethoxysilyl)propyl]polysulfide, and combinations thereof.

6. The dental composite material of claim 4, wherein at least a portion of the ceramic particles are coupled to the polymerizable resin by covalent binding between a moiety on the silane coupling agent and a moiety on the resin.

7. The dental composite material of claim 1, wherein the polymerizable resin comprises a methacrylate or dimethacrylate oligomer matrix.

8. The dental composite material of claim 1, wherein the polymerizable resin comprises a resin selected from the group consisting of bisphenol-A glycidyl methacrylate, urethane dimethacrylate, triethylene glycol dimethacrylate, and copolymers, and mixtures thereof.

9. The dental composite material of claim 1, wherein the antimicrobial agent is attached indirectly to the ceramic particles by means of a coupling agent overlying the fluorinated metal oxide surface.

10. The dental composite material of claim 9, wherein the coupling agent comprises a silane coupling agent.

11. A method of preparing the dental composite material of claim 1, comprising:
providing particulate ceramic comprising surfaces formed of a material comprising available hydroxyl groups;
treating the particulate ceramic with a fluorine-containing reagent to provide a fluorinated metal oxide on the particulate ceramic surfaces;
attaching one or more of the antimicrobial agents to the fluorinated metal oxide surface; and
dispersing the particulate ceramic within a polymerizable resin matrix.

12. The method of claim 11, further comprising reacting the particulate ceramic having the fluorinated metal oxide thereon with a coupling agent.

13. The method of claim 12, further comprising coupling the coupling agent to the polymerizable resin matrix.

14. The method of claim 11, wherein the attaching comprises attaching the one or more antimicrobial agents indirectly to the fluorinated metal oxide surface by means of a coupling agent overlying the fluorinated metal oxide surface.

15. The method of claim 11, further comprising attaching the one or more antimicrobial agents to a portion of the fluorinated metal oxide surfaces and coupling a portion of the fluorinated metal oxide surfaces to the resin matrix.

16. The method of claim 11, wherein the treating step comprises plasma treatment.

17. The method of claim 11, wherein the treating step comprises physical roughening or chemical etching of the implant surface prior to or at the same time as treating the implant with the fluorine-containing reagent.

18. The method of claim 11, wherein the fluorine-containing reagent is sulfur hexafluoride ($SF_6$).

19. A ceramic material comprising a fluorinated metal oxide surface with one or more antimicrobial agents attached thereto, wherein the antimicrobial agent is selected from the group consisting of silver acetate, silver benzoate, silver carbonate, silver ionate, silver iodide, silver lactate, silver laureate, silver nitrate, silver oxide, silver palmitate, silver protein, silver sulfadiazine, calcium oxide, calcium hydroxide, magnesium oxide, magnesium hydroxide, barium oxide, barium hydroxide, strontium oxide, strontium hydroxide alkali, chlorhexidine; 5-chloro-2(2-4-dichlorophenoxy)phenol), polyhexamethylenebiguanide hydrochloride (PHMB), doxycycline, metronidazole, thymol, encalypol, methyl salicylate, 4'-sulfamoylsulfanilanilide, 3-amino-6-(2-(5-nitro-2-furyl)vinyl)pyridiazine, transpseudomonic acid, xanthomycin, alpha-amino-p-toluene sulfonamide, alpha-azido benzyl penicillin, penicillin O, penicillin N, monopropionyl erthromycin, erythromycin 9(O-((2-methoxyethoxy)methyl) oxime; 1,1'-hexamethlene bis(5-(p-chlorophenyl)biguanide), cetyl pyridinium chloride; benzalkonium chloride, cetyl pyridinium bromide, 2,4,4'-trichloro-2'-hydroxy-diphenyl ether, antimicrobial peptides, and combinations thereof.

20. The ceramic material of claim 19, wherein the one or more antimicrobial agents are attached indirectly to the ceramic material by means of a coupling agent overlying the fluorinated metal oxide surface.

21. The ceramic material of claim 20, wherein the coupling agent comprises a silane coupling agent.

22. The ceramic material of claim 21, wherein the silane coupling agent is selected from the group consisting of 3-methacryloyloxypropyltrimethoxysilane, 3-trimethoxysilylpropylmethacrylate, 3-acryloyloxypropyltrimethoxysilane, 3-isocyanatopropyltriethoxysilane, N-[3-(trimethoxysilyl)propylethylenediamine], 3-mercaptopropyltrimethoxysilane, bis[3-(triethoxysilyl)propyl]polysulfide, and combinations thereof.

23. The ceramic material of claim 19, wherein the ceramic material is a medical implant or a particulate ceramic.

24. The ceramic material of claim 19, wherein the ceramic material comprises a material selected from the group consisting of zirconia, alumina, titania, and chromium-oxide-based materials.

25. A method of preparing the surface of a ceramic implant, comprising:

providing a ceramic implant comprising a surface formed of a material comprising available hydroxyl groups;

treating the ceramic implant with a fluorine-containing reagent to provide a fluorinated metal oxide on the surface; and attaching one or more antimicrobial agents to at least a portion of the fluorinated metal oxide, wherein the antimicrobial agents are selected from the group consisting of silver acetate, silver benzoate, silver carbonate, silver ionate, silver iodide, silver lactate, silver laureate, silver nitrate, silver oxide, silver palmitate, silver protein, silver sulfadiazine, calcium oxide, calcium hydroxide, magnesium oxide, magnesium hydroxide, barium oxide, barium hydroxide, strontium oxide, strontium hydroxide alkali, chlorhexidine; 5-chloro-2(2-4-dichlorophenoxy)phenol), polyhexamethylenebiguanide hydrochloride (PHMB), doxycycline, metronidazole, thymol, encalypol, methyl salicylate, 4'-sulfamoylsulfanilanilide, 3-amino-6-(2-(5-nitro-2-furyl)vinyl)pyridiazine, transpseudomonic acid, xanthomycin, alpha-amino-p-toluene sulfonamide, alpha-azido benzyl penicillin, penicillin O, penicillin N, monopropionyl erthromycin, erythromycin 9(O-((2-methoxyethoxy)methyl) oxime; 1,1'-hexamethlene bis(5-(p-chlorophenyl)biguanide), cetyl pyridinium chloride; benzalkonium chloride, cetyl pyridinium bromide, 2,4,4'-trichloro-2'-hydroxy-diphenyl ether, antimicrobial peptides, and combinations thereof.

26. The method of claim 25, wherein the attaching step comprises indirectly attaching the one or more antimicrobial agents by means of a coupling agent overlying the fluorinated metal oxide surface.

27. The method of claim 25, wherein the surface of the ceramic implant comprises zirconia, alumina, titania, chromium oxide, or a combination thereof.

28. The method of claim 25, further comprising applying dental cement to attach at least a portion of the fluorinated metal oxide to a dental component selected from the group consisting of dental implants, crowns, bridges, fillings, veneers, inlays, onlays, endodontic devices, or orthodontic brackets.

29. The method of claim 28, wherein the dental component comprises a surface comprising natural tooth, metal, porcelain fused to metal, porcelain, ceramic, resin, or a combination thereof.

30. The method of claim 25, wherein the coupling agent is a silane coupling agent selected from the group consisting of 3-methacryloyloxypropyltrimethoxysilane, 3-trimethoxysilylpropylmethacrylate, 3-acryloyloxypropyltrimethoxysilane, 3-isocyanatopropyltriethoxysilane, N-[3-(trimethoxysilyl)propylethylenediamine], 3-mercaptopropyltrimethoxysilane, bis[3-(triethoxysilyl)propyl]polysulfide, and combinations thereof.

31. The method of claim 25, wherein the treating step comprises plasma treatment.

32. The method of claim 25, wherein the treating step comprises physical roughening or chemical etching of the implant surface prior to or at the same time as treating the implant with the fluorine-containing reagent.

33. The method of claim 25, wherein the fluorine-containing reagent is sulfur hexafluoride ($SF_6$).

* * * * *